(12) United States Patent
Haick

(10) Patent No.: US 11,243,186 B2
(45) Date of Patent: Feb. 8, 2022

(54) CHEMICALLY SENSITIVE FIELD EFFECT TRANSISTORS AND USES THEREOF IN ELECTRONIC NOSE DEVICES

(71) Applicant: TECHNION RESEARCH AND DEVELOPMENT FOUNDATION LTD., Haifa (IL)

(72) Inventor: Hossam Haick, Haifa (IL)

(73) Assignee: TECHNION RESEARCH AND DEVELOPMENT FOUNDATION LTD., Haifa (IL)

(*) Notice: Subject to any disclaimer, the term of this patent is extended or adjusted under 35 U.S.C. 154(b) by 294 days.

(21) Appl. No.: 16/000,121

(22) Filed: Jun. 5, 2018

(65) Prior Publication Data
US 2018/0282155 A1    Oct. 4, 2018

Related U.S. Application Data

(63) Continuation of application No. 12/669,965, filed as application No. PCT/IL2008/001028 on Jul. 24, 2008, now Pat. No. 10,011,481.
(Continued)

(51) Int. Cl.
*G01N 27/414*    (2006.01)
*H01L 29/772*    (2006.01)
(Continued)

(52) U.S. Cl.
CPC .......... *G01N 27/4148* (2013.01); *B82Y 15/00* (2013.01); *G01N 27/4146* (2013.01);
(Continued)

(58) Field of Classification Search
None
See application file for complete search history.

(56) References Cited

U.S. PATENT DOCUMENTS

| 5,092,218 A | 3/1992 | Fine |
| 5,109,691 A | 5/1992 | Corrigan |

(Continued)

FOREIGN PATENT DOCUMENTS

| WO | 2000/000808 | 1/2000 |
| WO | 2005004204 | 1/2005 |
| WO | 2008030395 | 3/2008 |

OTHER PUBLICATIONS

Assad, Ossama and Haick, Hossam (2008) Stable scaffolds for reacting Si nanowires with further organic functionalities while preserving Si—C passivation of surface sites. J. Am. Chem. Soc., 130(52)117670-17671.
(Continued)

*Primary Examiner* — Neil N Turk
(74) *Attorney, Agent, or Firm* — Browdy and Neimark, PLLC

(57) ABSTRACT

A system having an electronic device. The electronic device has an array of chemically sensitive sensors. The sensors detect volatile organic compounds and have field effect transistors. The transistors have non-oxidized, functionalized silicon nanowires. The nanowires have surface Si atoms. The device has a plurality of functional groups that form a direct Si—C bond with the silicon nanowires, wherein Si is a surface Si atom and C is a carbon atom of the functional group. The functional groups are selected from the group consisting of: alkyl, cycloalkyl, alkenyl, alkynyl, aryl, heterocyclyl, heteroaryl, alkylaryl, alkylalkenyl, alkylalkynyl, alkylcycloalkyl, alkylheterocyclyl and alkylheteroaryl groups, and derivatives thereof, wherein said functional groups are other than methyl and 1-butyl. The plurality of functional groups are attached to 50-100% of the surface Si atoms.

4 Claims, 21 Drawing Sheets

Related U.S. Application Data

(60) Provisional application No. 61/056,073, filed on May 27, 2008, provisional application No. 60/951,476, filed on Jul. 24, 2007.

(51) Int. Cl.
| | |
|---|---|
| *B82Y 15/00* | (2011.01) |
| *B82Y 30/00* | (2011.01) |
| *G01N 33/543* | (2006.01) |
| *H01L 29/08* | (2006.01) |
| *G01N 33/00* | (2006.01) |
| *G01N 33/497* | (2006.01) |

(52) U.S. Cl.
CPC ........ *G01N 33/54373* (2013.01); *B82Y 30/00* (2013.01); *G01N 33/0034* (2013.01); *G01N 2033/4975* (2013.01); *H01L 29/0843* (2013.01); *H01L 29/772* (2013.01); *Y10S 977/70* (2013.01); *Y10S 977/742* (2013.01)

(56) References Cited

U.S. PATENT DOCUMENTS

| | | | |
|---|---|---|---|
| 5,585,575 | A | 12/1996 | Corrigan |
| 5,698,089 | A | 12/1997 | Lewis |
| 5,801,297 | A | 9/1998 | Misfud |
| 6,173,602 | B1 | 1/2001 | Moseley |
| 6,319,724 | B1 | 11/2001 | Lewis |
| 6,411,905 | B1 | 6/2002 | Guoliang |
| 6,423,272 | B1 | 7/2002 | Boden |
| 6,467,333 | B2 | 10/2002 | Lewis |
| 6,571,649 | B2 | 6/2003 | Sakairi |
| 6,606,566 | B1 | 8/2003 | Sunshine |
| 6,609,068 | B2 | 8/2003 | Cranley |
| 6,620,109 | B2 | 9/2003 | Hanson, III |
| 6,703,241 | B1 | 3/2004 | Sunshine |
| 6,746,960 | B2 | 6/2004 | Goodman |
| 6,767,732 | B2 | 7/2004 | Alocilja |
| 6,773,926 | B1 | 8/2004 | Freund |
| 6,820,012 | B2 | 11/2004 | Sunshine |
| 6,839,636 | B1 | 1/2005 | Sunshine |
| 6,840,120 | B2 | 1/2005 | Sakairi |
| 6,841,391 | B2 | 1/2005 | Lewis |
| 6,872,786 | B2 | 3/2005 | Murray |
| 7,052,854 | B2 | 5/2006 | Melker |
| 7,101,761 | B2 | 9/2006 | Chau |
| 7,129,554 | B2 | 10/2006 | Lieber |
| 7,151,209 | B2 | 12/2006 | Empedocles |
| 7,224,345 | B2 | 5/2007 | Kawell |
| 7,335,259 | B2 | 2/2008 | Hanrath |
| 7,469,076 | B2 | 12/2008 | Carlson |
| 8,048,377 | B1 | 11/2011 | Zhou |
| 2002/0117659 | A1 | 8/2002 | Lieber |
| 2002/0119513 | A1 | 8/2002 | Alocilja |
| 2004/0136866 | A1 | 7/2004 | Pontis |
| 2005/0029678 | A1 | 2/2005 | Hanrath |
| 2005/0032100 | A1 | 2/2005 | Heath |
| 2005/0136585 | A1 | 6/2005 | Chau |
| 2006/0191319 | A1 | 8/2006 | Kurup |
| 2006/0231420 | A1 | 10/2006 | Garzon |
| 2006/0277974 | A1 | 12/2006 | Gouma |
| 2006/0278866 | A1 | 12/2006 | Star |
| 2007/0094179 | A1 | 4/2007 | Ridi |
| 2007/0095678 | A1 | 5/2007 | West |
| 2008/0116490 | A1 | 5/2008 | Stewart |
| 2010/0087013 | A1 | 4/2010 | Lieber |
| 2010/0112546 | A1 | 5/2010 | Lieber |
| 2010/0323925 | A1 | 12/2010 | Gabriel |

OTHER PUBLICATIONS

Bunimovich, Yuri L. et al., (2006) Quantitative real-time measurements of DNA hybridization with alkylated nonoxidized silicone nanowires in electrolyte solution. Journal of The American Chemical Society 128(50)116323-16331.
Chen, Xing et al., (2005) Meas. Sci. Technol. 16, 1535-1546.
Cui, Yi et al., (2001) Nanowire nanosensors for highly sensitive and selective detection of biological and chemical species. Science 293:1289-1292.
Haick H. et al., (2006) Electrical characteristics and chemical stability of non-oxidized, methyl-terminated silicon nanowires. J. Am. Chem. Soc. 128(28):8990-8991.
Hassler, K. and Koll, W. (1995) J. Organom et al. Chem. 487(1-2):223-226.
Huang, Xing-Jiu and Choi, Yang-Kyu (2007) Chemical sensors based on nanostructured materials. Sensors and Actuators B 122(2):659-671.
Juang, Agnes et al., (2001) Formation of Covalently-Attached Polymer Overlayers on Si(111) Surfaces Using Ring-Opening Metathesis. Polymerization Methods Langmuir 17:1321-1323.
Kawase, Masaya et al., (2000) Immobilization of ligand-modified polyamidoamine dendrimer for cultivation of hepatoma cells. Artificial Organs 24(1):18-22.
Lupke, G. (1999) Characterization of semiconductor interfaces by second-harmonic generation. Surf. Sci. Rep. 35:75-161.
McAlpine, Michael C. et al., (2007) Highly ordered nanowire arrays on plastic substrates for ultrasensitive flexible chemical sensors. Nature Materials 6(5):379-384.
Patolsky, Fernando and Lieber, Charles M. (2005) Materials Today 8:20-28.
Pavlou, Alexandros K. et al., (2004) Detection of *Mycobacterium tuberculosis* (TB) in vitro and in situ using an electronic nose in combination with a neural network system. Biosensors & Bioelectronics 20(3):538-544.
Puniredd, Sreenivasa Reddy et al., (2008) Highly stable organic monolayers for reacting Silicon with further functionalities: The effect of the C—C bond nearest the Silicon surface. J. Am. Chem. Soc. 130(41):13727-13734.
Stern, Eric et al., (2007) Label-free immunodetection with CMOS-compatible semiconducting nanowires. Nature 445(7127):519-522.
Toal, Sarah J. and Trogler, William C. (2006) Polymer sensors for nitroaromatic explosives detection. J. Mater. Chem. 16(28):2871-2883.
Wang, Joseph (2004) Microchip devices for detecting terrorist weapons. Analy Chimi Acta 507(1):3-10.
Webb, Lauren J.and Lewis, Nathan S. (2003) Comparison of the electrical properties and chemical stability of crystalline silicon surfaces alkylated using Grignard reagents or Olefins with Lewis acid catalysts. Journal of Physical Chemistry B 107(23):5404-5412.
ISR of PCT/IL2008/001028—dated Dec. 4, 2008.
IPRP of PCT/IL2008/001028—dated Feb. 4, 2010.
Bashouti et al., (2008) Chemical Passivation of Silicon Nanowires with C1-C6 Alkyl Chains through Covalent Si—C Bonds. J Phys Chem 112(49): 19168-19172.
Haick et al., (2006) Electrical Characteristics and Chemical Stability of Non-Oxidized, Methyl-Terminated Silicon Nanowires. J Am Chem Soc 128(28): S1-S3 Supporting Information.
Page 63, paragraphs 3 and 4 of Zhang, X. G. (2001), Electrochemistry of Silicon and its Oxide, Kluwer Academic/Plenum Publishers, 0-306-46541-8, New York, Chapter 2.
N. Herzer, S. Hoeppener and U. S. Schubert, Chem. Commun., 2010, 46, 5634-5652.
S. Ciampi, J. B. Harper and J. J. Gooding, Chem. Soc. Rev., 2010, 39, 2158-2183.
Assad et al., (2008) Stable Scaffolds for Reacting Si Nanowires with Further Organic Functionalities while Preserving Si—C Passivation of Surface Sites. J Am Chem Soc 130(52): 17670-17671.
Puniredd et al., (2008) Highly stable organic modification of Si(111) surfaces: towards reacting Si with further functionalities while preserving the desirable chemical properties of full Si—C atop site terminations. J Am Chem Soc 130(29): 9184-9185.
Bi et al., (2008) Development of electrochemical calcium sensors by using silicon nanowires modified with phosphotyrosine. Biosensors and Bioelectronics 23(10): 1442-1448 (8 pages).

(56) References Cited

OTHER PUBLICATIONS

Buriak (2002) Organometallic Chemistry on Silicon and Germanium Surfaces. Chemical Reviews 102(5): 1271-1308 (38 pages).

Ermanok et al., (2013) Discriminative Power of Chemically Sensitive Silicon Nanowire Field Effect Transistors to Volatile Organic Compounds. ACS Appl Mater Interfaces 5(21): 11172-11183 (13 pages).

Luo et al., (2009) Silicon nanowire sensors for Hg2+ and Cd2+ ions. Applied Physics Letters 94: 193101; 3 pages (4 pages with cover sheet).

Paska and Haick (2012) Interactive Effect of Hysteresis and Surface Chemistry on Gated Silicon Nanowire Gas Sensors. ACS Appl Mater Interfaces 4(5): 2604-2617 (20 pages).

Paska et al., (2011) Enhanced Sensing of Nonpolar Volatile Organic Compounds by Silicon Nanowire Field Effect Transistors. ACS Nano 5(7): 5620-5626 (8 pages).

Puniredd et al., (2011) Catalyst-Free Functionalization for Versatile Modification of Nonoxidized Silicon Structures. Langmuir 27(8): 4764-4771 (8 pages).

Wang and Haick (2013) Effect of Chain Length on the Sensing of Volatile Organic Compounds by means of Silicon Nanowires. ACS Appl Mater Interfaces 5(12): 5748-5756 (10 pages).

Wang and Haick (2013) Effect of Functional Groups on the Sensing Properties of Silicon Nanowires toward Volatile Compounds. ACS Appl Mater Interfaces 5(6): 2289-2299 (14 pages).

Zhang et al., (2008) Highly sensitive measurements of PNA-DNA hybridization using oxide-etched silicon nanowire biosensors. Biosensors and Bioelectronics 23(11): 1701-1707 (7 pages).

Zheng et al., (2005) Multiplexed electrical detection of cancer markers with nanowire sensor arrays. Nat Biotechnol 23(10): 1294-301 (8 pages).

CHEMICALLY SENSITIVE FIELD EFFECT TRANSISTORS AND USES THEREOF IN ELECTRONIC NOSE DEVICES

FIELD OF THE INVENTION

The present invention relates to an electronic device for detecting volatile organic compounds with high sensitivity. In particular, the present invention provides chemically sensitive field effect transistors of non-oxidized, functionalized silicon nanowires and methods of use thereof.

BACKGROUND OF THE INVENTION

Electronic nose devices perform odor detection through the use of an array of cross-reactive sensors in conjunction with pattern recognition methods. In contrast to the "lock-and-key" model, each sensor in the electronic nose device is widely responsive to a variety of odorants. In this architecture, each analyte produces a distinct signature from the array of broadly cross-reactive sensors. This configuration allows to considerably widen the variety of compounds to which a given matrix is sensitive, to increase the degree of component identification and, in specific cases, to perform an analysis of individual components in complex multi-component mixtures. Pattern recognition algorithms can then be applied to the entire set of signals, obtained simultaneously from all the sensors in the array, in order to acquire information on the identity, properties and concentration of the vapor exposed to the sensor array. Various algorithms and computer controlled systems for olfactometry known in the art are disclosed for example in U.S. Pat. Nos. 6,411,905, 6,606,566, 6,609,068, 6,620,109, 6,767,732, 6,820,012, and 6,839,636, among others.

Micro-organisms produce patterns of volatile organic compounds (VOCs) that are affected by the type and age of culture media. Patterns of VOCs can also be used as biomarkers of various diseases, e.g., acute asthma, uremia, cirrhosis, cystinuria, trimethylaminuria, etc. These disease biomarkers can be found in the bodily fluids of a patient, including in the serum, urea, and breath. Characteristic VOCs display different patterns at different stages of the disease.

Various devices and methods for VOC detection and analysis are disclosed, for instance, in U.S. Pat. Nos. 6,319,724, 6,411,905, 6,467,333, 6,606,566, 6,609,068, 6,620,109, 6,703,241, 6,767,732, 6,820,012, 6,839,636, 6,841,391, and in U.S. Pat. Appl. No. 2001/0041366. A transition metal oxide gas sensor is disclosed and described in U.S. Pat. No. 6,173,602.

Excluding a few individual instances, the detection levels of these devices are in the range of 1-100 parts per million (ppm). In order to detect VOCs with higher sensitivity, pre-concentrating the vapors to be detected prior to measurement is required. Consequently, real-time measurement of minute quantities of VOCs remains a challenge.

The use of Gas-Chromatography (GC), GC-lined Mass-Spectroscopy (GC-MS), Quartz Crystal Microbalance (QCM) as well as other comparable techniques for analysis of volatile biomarkers indicative of certain diseases, is impeded by several factors. These factors include the need for expensive equipment, the degree of expertise required to operate such instruments, the length of time required to obtain data acquisition, and other technical problems in sampling, data analysis, etc. Mostly, the GC-MS technique is limited to the ppm level of concentrations, while many disease biomarkers are present at concentration levels of less than one part per billion (ppb).

Similar to olfactory receptors, increased sensitivity as well as on/off rates of chemical sensors is typically achieved by reducing the dimensions of the sensing apparatus. Chemical sensors made of nanomaterials are more sensitive, more controlled, and more suitable to differentiate between subtle differences in mixtures of volatile biomarkers. Silicon nanowires (Si NWs) offer unique opportunities for signal transduction associated with selective recognition of biological or chemical species of interest.

Oxide-coated silicon nanowire field effect transistors (Si NW FETs) have been modified with amino siloxane functional groups to impart high sensitivity towards pH (Patolsky and Lieber, Mater. Today, 2005, 8: 20-28). The Si NW field effect transistors were further modified with a variety of biological receptors to selectively detect biological species in solution. Oxide-coating of a Si NW is believed to induce trap states at the Si/Si-oxide interface thus acting as a dielectric layer. This in turn lowers and consequently limits the effect of gate voltage on the transconductance of Si NW field effect transistors. This limitation affects the response of sensors based on oxide-coated Si NW field effect transistors to their environment. In a typical $SiO_2$-coated Si NW field effect transistor, the transconductance responds weakly to the applied gate voltage, $V_g$, where conductivity changes by two orders of magnitude between $V_g=-5V$ and $V_g=+5$ V, with no significant on/off state transition within this gate-bias region. This behavior is compatible with the characteristics of oxidized Si wherein both the $Si/SiO_2$ interface and the $SiO_2$ surface defects trap and scatter carriers, and as a result, decrease the effect of $V_g$ (Lupke, Surf Sci. Rep., 1999, 35:75-161). On the contrary, devices that are based on non-oxidized Si NWs as well as those based on macroscopic planar Si (111) surfaces, exhibit low interface state density. Yet, non-oxidized Si NWs as well as Si surfaces that are terminated with hydrogen tend to undergo oxidation upon exposure to ambient conditions, resulting in the formation of defects in the sensors.

It has been reported by the inventor of the present invention, that Si NWs modified by covalent binding to a methyl functional group, show atmospheric stability, high conductance values, and less surface defects. These methyl functionalized Si NWs were shown to form air-stable Si NW field effect transistors having on-off ratios in excess of $10^5$ over a relatively small (±2 V) gate voltage swing (Haick et al., J. Am. Chem. Soc., 2006, 128: 8990-8991). However, exposure of these methyl-functionalized devices to analytes barely provides sensing responses, most probably due to the low ability of the methyl groups to adsorb vapor/liquid analytes. Further modifications of the methyl functional groups for sensing applications at minute concentration down to the ppb levels, are not feasible.

Hence, there is an unmet need for a highly sensitive reliable device to analyze mixtures of volatile organic compounds. Furthermore, there is an unmet need for an inexpensive, efficient, convenient, reliable, and portable device to analyze mixtures of volatile biomarkers.

SUMMARY OF THE INVENTION

The present invention provides an electronic device for detecting volatile organic compounds (VOCs), which is more sensitive than known systems serving a similar purpose. The device disclosed herein, comprises field effect transistors of non-oxidized functionalized silicon nanowires (Si NWs). The present invention further relates to a system comprising an electronic device comprising an array of chemically sensitive sensors in conjunction with learning and pattern recognition algorithms. The learning and pattern recognition algorithms receive sensor output signals which are analyzed using methods such as artificial neural networks and principal component analysis and are subsequently compared to stored data. Methods of preparing said devices and methods of use thereof for detecting and quantifying specific compounds are disclosed as well.

The invention is based in part on the unexpected finding that non-oxidized silicon nanowire-based sensors provide improved sensing capabilities. The lack of oxide layer on the surface of the nanowires improves the sensitivity of the detectors thus providing the detection of minute quantities of volatile organic compounds. The detection of minute quantities of volatile organic compounds enables the identification of biomarkers from body secretions without the need for pre-concentration.

According to a first aspect, the present invention provides an electronic device comprising at least one chemically sensitive sensor for the detection of volatile organic compounds, wherein the chemically sensitive sensor comprises field effect transistors comprising non-oxidized, functionalized silicon nanowires (Si NWs), wherein the functional group is other than methyl.

According to another aspect, the present invention provides a system comprising an electronic device for detecting volatile organic compounds, wherein said electronic device comprises an array of chemically sensitive sensors comprising field effect transistors of non-oxidized, functionalized silicon nanowires (Si NWs), and learning and pattern recognition analyzer wherein said learning and pattern recognition analyzer receives sensor signal outputs and compares them to stored data.

In one embodiment, the electronic devices of the present invention detect volatile organic compounds with sensitivity below one part per million (ppm). In another embodiment, the electronic devices detect volatile organic compounds with sensitivity of less than 100 parts per billion (ppb). In yet another embodiment, the electronic devices disclosed herein detect volatile organic compounds with sensitivity of one part per billion (ppb) or less.

In some embodiments, the Si NW field effect transistors are manufactured in a top-down approach. In alternative embodiments, the Si NW field effect transistors are manufactured in a bottom-up approach.

According to certain embodiments, the surface of the Si NWs is modified with a plurality of compounds via a direct Si—C bond. In currently preferred embodiments, these compounds form film layers on the surface of the nanowires, without intervening oxide layers. For example, the present invention uses compounds that attach through Si—C—C, Si—C=C, and Si—C≡C bonds.

In other embodiments, the functional groups which are used to modify the surface of the nanowires include, but are not limited to: alkyl, cycloalkyl, alkenyl, alkynyl, aryl, heterocyclyl, heteroaryl, alkylaryl, alkylalkenyl, alkylalkynyl, alkylcycloalkyl, alkylheterocyclyl and alkylheteroaryl groups; combinations and derivatives thereof. The functional groups can be substituted by one or more halogens selected from the group consisting of fluorine, chlorine, bromine, and iodine. Additional substituents are haloalkyl, acyl, amido, ester, cyano, nitro, and azido.

In certain embodiments, the functional groups used to modify the surface of the nanowires include, but are not limited to, ethyl, isopropyl, tert-butyl, hexyl, octyl, and phenyl, cyclic $C_6$ hydrocarbonyl, 1,3-cyclohexadienyl, 1,4-cyclohexadienyl, cyclohexyl, H-terminated bicyclo[2.2.2] octyl, Cl-terminated bicyclo[2.2.2]octyl, and combinations thereof.

In other embodiments, the functional groups used to modify the surface of the nanowires include, but are not limited to, 1-pentyl, 1-dodecyl, 2-hexynyl, 1-octenyl, 1-pentenyl, 1-dodecenyl, 1-octadecenyl, cis-2-pentenyl, trans-2-hexenyl, 2,3-dimethyl-2-pentenyl, styrenyl and five-, six-, eight-membered ring derivatives thereof; and combinations thereof.

In yet other embodiments, the functional groups used to modify the surface of the nanowires include, but are not limited to, phenylacetylenyl, 1-phenyl-2-(trimethylsilyl) acetylenyl, 1-octynyl, dodec-1-ynyl, 1-trimethylsilyldodec-1-ynyl, pentynyl, diphenylphosphino-acetylenyl, arynyl, diphenyl-phosphinoethynyl, and combinations thereof.

In certain embodiments, the surface of the nanowires is modified with ultra thin polymer films of e.g. polypropylene or polynorbornene. In one embodiment, these polymer films are grown via layer-by-layer or ring-opening metathesis polymerization approaches. According to currently preferred embodiments, the polymer films have thicknesses ranging from about 1 nm to about 500 nm.

The present invention also encompasses an electronic device designated for the detection of volatile organic compounds, comprising an array of chemically sensitive sensors. The array of sensors comprises a plurality of sensors between 2 to 1000 sensors, more preferably between 2 to 500 sensors, even more preferably between 2 to 250 sensors, and most preferably between 2 to 125 sensors in an array.

According to another aspect, the present invention further provides a system comprising an electronic device designated for the detection of volatile organic compounds, comprising an array of chemically sensitive sensors in conjunction with a learning and pattern recognition analyzer, wherein said learning and pattern recognition analyzer receives sensor output signals and compares them to stored data. The learning and pattern recognition analyzer may utilize various algorithms including algorithms based on artificial neural networks, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods such as principal component analysis (PCA), partial least squares (PLS), multiple linear regression (MLR), principal component regression (PCR), discriminant function analysis (DFA) including linear discriminant analysis (LDA), cluster analysis including nearest neighbor, and the like.

According to another aspect, the present invention provides a method for determining at least one of the composition and concentration of volatile organic compounds in a sample using the electronic devices of the present invention, comprising the steps of: (a) providing a system comprising an electronic device for detecting volatile compounds comprising an array of chemically sensitive sensors of non-oxidized, functionalized silicon nanowire field effect transistors, and a learning and pattern recognition analyzer, wherein said learning and pattern recognition analyzer receives sensor output signals from the electronic device and compares them to stored data, (b) exposing the sensor array of said electronic device to the sample, and (c) using pattern recognition algorithms to detect the presence of said volatile compounds in the sample.

According to another aspect, the present invention provides a method for diagnosing a disease in a subject, comprising: (a) providing a system comprising an electronic device for detecting volatile organic compounds comprising an array of chemically sensitive sensors of non-oxidized, functionalized silicon nanowire field effect transistors, and a learning and pattern recognition analyzer, wherein said learning and pattern recognition analyzer receives sensor output signals and compares them to stored data, (b) exposing the sensor array of said electronic device to the breath of a subject, or to the headspace of a container in which a bodily fluid of the subject has been deposited, and (c) using pattern recognition algorithms to detect volatile organic compounds, in the sample indicative of a disease in said subject.

In yet another aspect, the present invention provides the use of an electronic device comprising an array of chemically sensitive sensors wherein the chemically sensitive sensors comprise field effect transistors comprising non-oxidized, functionalized silicon nanowires, and a learning and pattern recognition analyzer, wherein said learning and pattern recognition analyzer receives sensor output signals and compares them to stored data, for the preparation of an apparatus for detecting volatile organic compounds. In a currently preferred embodiment, the use disclosed herein is designated towards detecting volatile organic compounds that are indicative of a disease in a subject.

The present invention further provides a system for diagnosing a disease in a subject comprising exposing an electronic device comprising an array of chemically sensitive sensors wherein the chemically sensitive sensors comprise field effect transistors comprising non-oxidized, functionalized silicon nanowires to the breath of a subject, or to the headspace of a container in which a bodily fluid of the subject has been deposited, and using pattern recognition algorithms to receive sensor output signals and compare them to stored data.

Bodily fluids or secretions that can be tested by this method include, but are not limited to, serum, urine, feces, sweat, vaginal discharge, saliva and sperm. Many diseases or disorders can be diagnosed by the methods and systems of the invention, including, but not limited to, oral infections, periodontal diseases, halitosis, ketosis, yeast infections, pneumonia, lung infections, cancer, sexually transmitted diseases, vaginitis, nephritis, bilirubin production, renal disease, cardiovascular disease, hypercholesterolemia, gastrointestinal infections, diabetes, and phenylketonuria. According to a preferred embodiment, the present invention provides a method of diagnosing cancer.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention provides an electronic device for detecting volatile organic compounds at levels as low as 100 parts per billion (ppb) or less. The electronic device comprises chemically sensitive sensors comprising field effect transistors of non-oxidized, functionalized silicon nanowires. The invention further provides a system comprising an array of sensors and pattern recognition analyzer which uses algorithms, such as principal component analysis and neural network algorithms, to classify and detect a wide variety of volatile organic compounds. Further provided are methods of use thereof in detecting biomarkers indicative of certain medical disorders.

Figure 1:
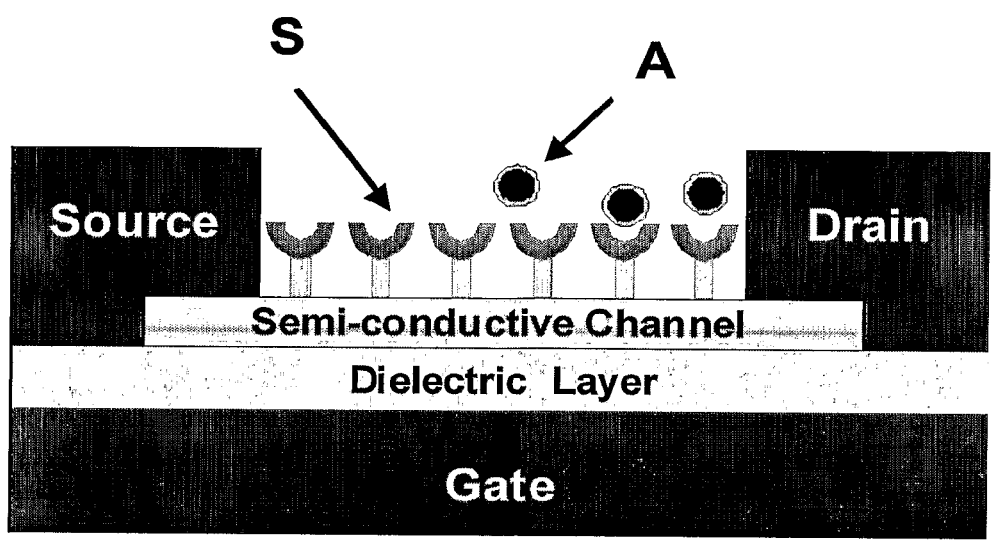
FIG. 1 is a schematic representation of a Si NW field effect transistor arrangement used for chemical sensing without a reference electrode. The molecular layer is directly bonded to the semiconductor and the gating is done from the back. 'A' represents analyte molecules, and 'S' represents sensing molecules.
Figure 2:
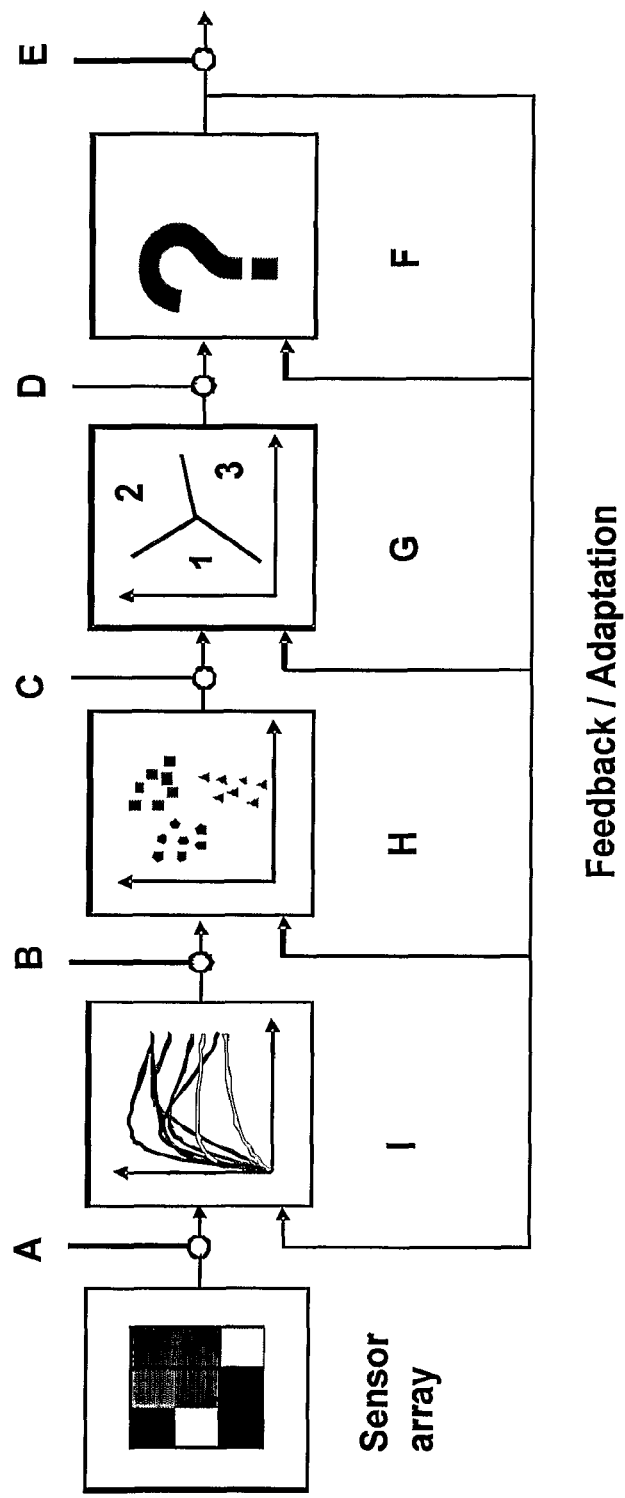
FIG. 2 is a schematic diagram illustrating the differentiation between odorants using an array of broadly-cross reactive sensors, in which each individual sensor responds to a variety of odorants, in conjugation with pattern recognition algorithms to allow classification. 'A'—raw measurements, 'B'—normalized measurements, 'C'—feature vector, 'D'—odor class (confidence level), 'E'—post processed odor class, 'F'—decision making, 'G'—classification, 'H'—dimensionality reduction, and 'I'—signal preprocessing.

According to the principles of the present invention, the electronic devices disclosed herein comprise chemically sensitive field effect transistors (FETs) of non-oxidized, functionalized silicon nanowires (Si NWs; FIG. 1). Sensing is obtained through adsorption of vapors to provide changes in electrical resistance. The electrical signals are then conveyed to a pattern recognition analyzer to generate qualitative identification and preferably quantitative analysis of desired volatile organic compounds (VOCs). A schematic diagram of the differentiation between odorants using the electronic nose devices is illustrated in FIG. 2. The array of sensors is exposed to a variety of VOCs to provide an electronic response vs. time ($2^{nd}$ box on the left). The dimensionality is then reduced wherein the data is represented by a new basis set ($f_2$ vs. $f_1$; $3^{rd}$ box on the left). This representation allows to classify the different odors (1, 2 & 3; $4^{th}$ box on the left). The procedure can be iteratively performed until satisfactory odor classification is achieved.

The present invention discloses for the first time, Si NW surfaces modified with Si—C bonds, wherein a significantly better coverage of the Si NWs with alkyl functional groups excluding methyl is obtained. Specifically, functionalization of the Si NWs with $C_2$-$C_{11}$ alkyl chains using a versatile two step chlorination/alkylation process, produces coverage in the range of 50-100% of the Si NW surface sites. This is approximately 1.5 times the coverage obtained for equivalent 2D Si (100) surfaces. The higher coverage provides Si NW surfaces having improved surface passivation and increased stability against oxidation. The alkylated Si NW surfaces of the present invention show high chemical stability at ambient conditions, as compared to alkylated 2D Si substrates.

Control over the surface chemistry of Si NWs is particularly important for the electrical performance of sensors composed of Si NW field effect transistors. The Si NWs of the present invention possess superior electrical properties in comparison to fully or partially oxidized Si NWs. These functionalized Si NWs can thus be used to fabricate electronic devices such as, but not limited to, Si-based photoelectrochemical cells with improved energy conversion. Additional use of oxide-free surfaces is for radial epitaxy on the nanowires to realize vertical P—N junctions for solar cells, or radial Si/Ge superlattices for application in optoelectronics.

Device

The electronic device described in the present invention uses finely-tuned arrays of surface-modified, non-oxidized Si NW field effect transistor-based sensors. The nanowires are approximately 5-120 nm in diameter, having a cylinder-like shape with a circle-like cross section, or equivalent dimensions wherein the nanowires have other cross sectional shapes including, but not limited to, trapezoidal, triangular, square, or rectangular. Si NWs having diameters (or equivalent dimensions for shapes other than cylinder) larger than 120 nm possess electrical/physical properties similar to planar Si. Si NWs with diameters (or equivalent dimensions for shapes other than cylinder) less than 5 nm consist mostly of $SiO_2$, with very low percentage of Si core. Thus, the Si NWs whose dimensions exceed the 5-120 nm range, are less suitable for sensing applications in accordance with the present invention.

Without being bound by any theory or mechanism of action, elimination of the intervening oxide layer from the Si NW field effect transistors provides increased sensitivity to the analytes to be detected. The chemical modification thus provides stable Si—C bonds even upon exposure to air and/or humidity, and further endows the Si NWs with chemical inertness and good electronic properties possibly due to the passivation of Si NW surface states. The modifications of the Si NW surfaces can be tailor-made to control the electrical properties of the Si NWs by, for example, utilizing adsorptive molecular dipoles on the Si NW surface, applying back gate voltage, and/or use of four-probe configuration. The modification further allows the control over the contact resistance between the Si NWs thus enabling the elimination of the electrodes, further providing the required sensitivity for detecting cancer biomarkers as well as other volatile organic compounds.

Formation of the Si NW Field Effect Transistors. The non-oxidized Si NW field effect transistor-based sensors of the present invention can be manufactured in two alternative manners: a bottom-up approach or a top-down approach.

In one embodiment of the invention, sensors of Si NW field effect transistors are manufactured through a bottom-up approach. Si NWs that are grown by, for example, vapor-liquid-solids, chemical vapor deposition (CVD), or oxide-assisted growth, are dispersed from organic solvent (e.g., isopropanol or ethanol) onto a doped Si substrate containing a thin film of dielectric layer (e.g., $SiO_2$, $ZrO_2$, etc.). The deposited Si NWs can be "bare" or "as-synthesized" ones, namely, with oxide layer and/or without being modified by organic molecules, or alternatively the deposited Si NWs can be non-oxidized and further possess various functionalities. The source/drain contacts to the Si NWs are introduced by either one of these techniques: electron beam lithography followed by evaporation of a metal that forms an ohmic contact, focused ion beam (FIB), and contact printing. The devices are then annealed to improve the quality of the contacts.

In another embodiment, the sensors are manufactured through a top-down approach. The fabrication process initiates from a SOI-SIMOX wafer, with thin top silicon layer, insulated from the silicon substrate by a buried silicon dioxide layer. Mask definition is performed by high resolution e-beam lithography. A bilayer PMMA resist is used. The exposure is performed using e-beam lithography with an acceleration voltage of 30 kV. The resist is then developed in a solution of MiBK:IPA 1:3. The pattern is transferred from the PMMA to the top $SiO_2$ layer by BHF etch. The central region, where the silicon is defined, is linked through small connections to the device leads. A 35 wt % KOH solution, saturated with isopropyl alcohol (IPA), is used. The nanowire then forms in the central region.

Surface modification of the Si NW Field Effect Transistors. Functionalizing the nanowires, whether before or after integration in the field effect transistor device, is performed through the use of reagents having different backbones and functional groups. Desired reagents are synthesized and attached to the Si NW surfaces, via Si—C bonds. The functional groups used include, but are not limited to, alkyl, cycloalkyl, alkenyl, alkynyl, aryl, heterocyclyl, heteroaryl, alkylaryl, alkylalkenyl, alkylalkynyl, alkylcycloalkyl, alkylheterocyclyl and alkylheteroaryl groups; combinations and derivatives thereof. The functional groups can be substituted by one or more halogens selected from the group consisting of fluorine, chlorine, bromine, and iodine. Other substitutions within the scope of the present invention include functionalization with haloalkyl, acyl, amido, ester, cyano, nitro, and azido groups.

An "alkyl" group refers to a saturated aliphatic hydrocarbon, including straight-chain, branched-chain and cyclic alkyl groups. In one embodiment, the alkyl is other than methyl. In another embodiment, the alkyl group has 2-12 carbons designated here as $C_2$-$C_{12}$-alkyl. In another embodiment, the alkyl group has 2-6 carbons designated here as $C_2$-$C_6$-alkyl. In another embodiment, the alkyl group has 2-4 carbons designated here as $C_2$-$C_4$-alkyl. The alkyl group may be unsubstituted or substituted by one or more groups selected from halogen, haloalkyl, acyl, amido, ester, cyano, nitro, and azido.

A "cycloalkyl" group refers to a non-aromatic mono- or multicyclic ring system. In one embodiment, the cycloalkyl group has 3-10 carbon atoms. In another embodiment, the cycloalkyl group has 5-10 carbon atoms. Exemplary monocyclic cycloalkyl groups include cyclopentyl, cyclohexyl, cycloheptyl and the like. An alkylcycloalkyl is an alkyl group as defined herein bonded to a cycloalkyl group as defined herein. The cycloalkyl group can be unsubstituted or substituted with any one or more of the substituents defined above for alkyl.

An "alkenyl" group refers to an aliphatic hydrocarbon group containing at least one carbon-carbon double bond including straight-chain, branched-chain and cyclic alkenyl groups. In one embodiment, the alkenyl group has 2-8 carbon atoms (a $C_{2-8}$ alkenyl). In another embodiment, the alkenyl group has 2-4 carbon atoms in the chain (a $C_{2-4}$ alkenyl). Exemplary alkenyl groups include ethenyl, propenyl, n-butenyl, i-butenyl, 3-methylbut-2-enyl, n-pentenyl, heptenyl, octenyl, cyclohexyl-butenyl and decenyl. An alkylalkenyl is an alkyl group as defined herein bonded to an alkenyl group as defined herein. The alkenyl group can be unsubstituted or substituted through available carbon atoms with one or more groups defined hereinabove for alkyl.

An "alkynyl" group refers to an aliphatic hydrocarbon group containing at least one carbon-carbon triple bond including straight-chain and branched-chain. In one embodiment, the alkynyl group has 2-8 carbon atoms in the chain (a $C_{2-8}$ alkynyl). In another embodiment, the alkynyl group has 2-4 carbon atoms in the chain (a $C_{2-4}$ alkynyl). Exemplary alkynyl groups include ethynyl, propynyl, n-butynyl, 2-butynyl, 3-methylbutynyl, n-pentynyl, heptynyl, octynyl and decynyl. An alkylalkynyl is an alkyl group as defined herein bonded to an alkynyl group as defined herein. The alkynyl group can be unsubstituted or substituted through available carbon atoms with one or more groups defined hereinabove for alkyl.

An "aryl" group refers to an aromatic monocyclic or multicyclic ring system. In one embodiment, the aryl group has 6-10 carbon atoms. The aryl is optionally substituted with at least one "ring system substituents" and combinations thereof as defined herein. Exemplary aryl groups include phenyl or naphthyl. An alkylaryl is an alkyl group as defined herein bonded to an aryl group as defined herein. The aryl group can be unsubstituted or substituted through available carbon atoms with one or more groups defined hereinabove for alkyl.

A "heteroaryl" group refers to a heteroaromatic system containing at least one heteroatom ring wherein the atom is selected from nitrogen, sulfur and oxygen. The heteroaryl contains 5 or more ring atoms. The heteroaryl group can be monocyclic, bicyclic, tricyclic and the like. Also included in this definition are the benzoheterocyclic rings. Non-limiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

A "heterocyclic ring" or "heterocyclyl" group refers to a five-membered to eight-membered rings that have 1 to 4 hetero atoms, such as oxygen, sulfur and/or in particular nitrogen. These five-membered to eight-membered rings can be saturated, fully unsaturated or partially unsaturated, with fully saturated rings being preferred. Preferred heterocyclic rings include piperidinyl, pyrrolidinyl pyrrolinyl, pyrazolinyl, pyrazolidinyl, morpholinyl, thiomorpholinyl, pyranyl, thiopyranyl, piperazinyl, indolinyl, dihydropyranyl, tetrahydrofuranyl, dihydrothiophenyl, tetrahydrothiophenyl, dihydropyranyl, tetrahydropyranyl, and the like. An alkylheterocyclyl is an alkyl group as defined herein bonded to a heterocyclyl group as defined herein. The heterocyclyl group can be unsubstituted or substituted through available atoms with one or more groups defined hereinabove for alkyl.

"Ring system substituents" refer to substituents attached to aromatic or non-aromatic ring systems including, but not limited to, H, halo, haloalkyl, $C_8$)alkyl, $(C_2$-$C_8)$alkenyl, $(C_2$-$C_8)$alkynyl, $(C_5$-$C_{10})$aryl, acyl, amido, ester, cyano, nitro, azido, and the like.

The term "halogen" or "halo" as used herein alone or as part of another group refers to chlorine, bromine, fluorine, and iodine. The term "haloalkyl" refers to an alkyl group having some or all of the hydrogens independently replaced by a halogen group including, but not limited to, trichloromethyl, tribromomethyl, trifluoromethyl, triiodomethyl, difluoromethyl, chlorodifluoromethyl, pentafluoroethyl, 1,1-difluoroethyl bromomethyl, chloromethyl, fluoromethyl, iodomethyl, and the like.

The term "acyl" as used herein encompasses groups such as, but not limited to, formyl, acetyl, propionyl, butyryl, pentanoyl, pivaloyl, hexanoyl, heptanoyl, octanoyl, nonanoyl, decanoyl, undecanoyl, dodecanoyl, benzoyl and the like. Currently preferred acyl groups are acetyl and benzoyl.

In particular, exemplary functional groups include, but are not limited to, (a) Methyl, ethyl, isopropyl, tert-butyl, hexyl, octyl, phenyl, cyclic $C_6$ hydrocarbonyl, 1,3-cyclohexadienyl, 1,4-cyclohexadienyl, cyclohexenyl, and H- and Cl-terminated bicyclo[2.2.2]octanyl. These functional groups bind to the Si surface through a Si—C—C bond. Without being bound by any theory or mechanism of action, the functionalization of the silicon nanowires with saturated non-oxidized functional groups such as alkyl and cycloalkyl is expected to provide high sensitivity towards biomarkers that adsorb between the chains of the molecular film.

(b) 1-pentynyl, 1-dodecynyl, 2-hexynyl, 1-octenyl, 1-pentenyl, 1-dodecenyl, 1-octadecenyl, cis-2-pentenyl, trans-2-hexenyl, 2,3-dimethyl-2-pentenyl, styrenyl and five-, six-, and eight-membered ring derivatives thereof. These functional groups bind to the Si surface through a Si—C=C bond, hence are expected to increase charge transfer through the attached backbones. Without being bound by any theory or mechanism of action, these functional groups are expected to provide increased sensitivity towards biomarkers that adsorb on the surface of the molecular film.

(c) phenylacetylenyl, 1-phenyl-2-(trimethylsilyl) acetylenyl, 1-octynyl, dodec-1-ynyl, 1-trimethylsilyldodec-1-ynyl, pentynyl, diphenylphosphino-acetylenyl, arynyl, and diphenyl-phosphinoethynyl. These functional groups bind to the Si surface through a Si—C≡C bridge, hence are expected to increase the charge transfer through the attached backbones. Additionally, these molecules equilibrate between the energy levels of the Si core interfaces and the energy levels of the molecular frontier orbitals effectively. Without being bound by any theory or mechanism of action, this provides another mechanism by which molecules can interact with the biomarkers and produce targeted sensitivity enhancements, especially for species which are adsorbed on top of the organic phase.

(d) ultra thin polymer films of e.g. polypropylene or polynorbornene. The attachment of polymeric chains to the Si NW surface can be performed via ruthenium ring-opening metathesis polymerization catalyst. This method allows to better control the thickness of the polymer that is attached to the silicon substrate. Currently preferable thicknesses range from about 0.9 nm to about 550 nm. Without being bound by any theory or mechanism of action, adjusting the thickness of the adsorbing layer to an optimal value is expected to increase the absorption of the targeted biomarkers, and, thus to enhance the sensitivity of the fabricated device.

Functionalization of the Si NW field effect transistors can be performed by several procedures, non-limiting examples of which will now be described.

Functionalization through Chlorination Route. Chlorinated Si (111) surfaces can be prepared by two different methods. In one chlorination method, an H-terminated sample is immersed into a saturated solution including $PCl_5$, $PBr_5$, and $PI_5$ that contains a few grains of radical initiator, such as $C_6H_5OOC_6H_5$. The reaction solution is heated to 90-100° C. for 45 minutes. In another chlorination method, an H-terminated sample is placed into a Schlenk reaction tube and transported to a vacuum line. Approximately 50-200 Torr of $Cl_{2(g)}$ is introduced through the vacuum line into the reaction tube, and the sample is illuminated for 30 seconds with a 366 nm ultraviolet light. Excess $Cl_{2(g)}$ is then removed under vacuum, and the flask is transported to the $N_{2(g)}$-purged flush box. The chlorine-terminated Si surfaces are molecularly modified by immersion in 1.0-3.0 molar R—MgX, where R signifies the backbone of molecules, and X=Cl, Br, or I. The reaction is performed for 1.5-16 hours at 70-80° C. wherein longer and bulkier molecular chains require longer reaction times. Excess THF, or other pertinent organic solvent, is added to all reaction solutions for solvent replacement. When the reaction ends, the samples are removed from the reaction solution and then rinsed in THF, $CH_3OH$, and occasionally TCE. Samples are then sonicated for about 5 minutes in $CH_3OH$ and $CH_3CN$ and dried.

Functionalization by Lewis Acid-Mediated Terminal Alkene Reduction. Freshly etched, H-terminated Si (111) surfaces are functionalized by immersion in approximately equal volumes of the molecule of interest and 1.0 M $C_2H_5AlCl_2$ in hexane at room temperature for 12 hours. Samples are removed from solution and rinsed in THF, $CH_2Cl_2$, and $CH_3OH$ consecutively, and then dried.

Functionalization by Electrochemical Reduction of R—MgI. Samples are mounted to a cell for surface functionalization reactions. Samples are then etched by filling the cell with 40% $NH_4F_{(aq)}$. After 20 minutes, the etching solution is removed and the cell is filled with $H_2O$ to rinse the sample surface. The $H_2O$ is then removed from the cell, and the sample is dried under a stream of $N_{2(g)}$. The cell is then moved into the $N_{2(g)}$-purged flush box for electrochemical modification. Each chamber of the electrochemical cell contains a section of Cu gauze that serves as a counter electrode. A single counter electrode is introduced into the solution. Molecular modification is performed using 3.0 M $CH_3MgI$ in diethyl ether by applying 0.1 mA·cm$^{-2}$ of constant anodic current density for 5 minutes with continuous stirring of the solution. After surface modification, the cell is rinsed with $CH_2Cl_2$ and $CH_3OH$, consecutively. The cell is then dismantled, and the top and bottom ohmic contacts are scribed off to leave behind only the portion of the wafer that had been exposed to the reaction solution. This wafer is rinsed further in $CH_3OH$, sonicated in $CH_3OH$, further sonicated in $CH_3CN$, and dried with a stream of $N_{2(g)}$.

Other modifying agents include ultra-thin monomer or polymer films, such as polypropylene or polynorbornene. Attachment of the polymers mentioned herein to the Si NW surface can be done via ruthenium ring-opening metathesis polymerization catalyst. In this manner, control over the thickness of the polymer attached to the silicon substrate from sub-nanometers to hundreds of nanometers is achieved.

Analysis

According to one embodiment, a method to determine the composition and concentration of volatile organic compounds (VOCs) in a sample, comprising exposure of the sensors of the electronic device to the sample and using pattern recognition algorithms in order to identify and possibly quantify desired VOCs in a given sample, is provided in the present invention. Thus, the electronic device of the present invention further includes a learning and pattern recognition analyzer. In practice, the analyzer receives signal outputs or patterns from the device and analyses them by various pattern recognition algorithms to produce an output signature. By comparing an unknown signature with a database of stored or known signatures, volatile organic compounds can be identified.

Algorithms for sample analysis, suitable for identifying and possibly quantifying VOCs include, but are not limited to, principal component analysis, Fischer linear analysis, neural network algorithms, genetic algorithms, fuzzy logic, pattern recognition, and the like. After analysis is completed, the resulting information can, for example, be displayed on display, transmitted to a host computer, or stored on a storage, device for subsequent retrieval.

Many of the algorithms are neural network based algorithms. A neural network has an input layer, processing layers and an output layer. The information in a neural network is distributed throughout the processing layers. The processing layers are made up of nodes that simulate the neurons by the interconnection to their nodes.

In operation, when a neural network is combined with a sensor array, the sensor data is propagated through the networks. In this manner, a series of vector matrix multiplications are performed and unknown analytes can be readily identified and determined. The neural network is trained by correcting the false or undesired outputs from a given input. Similar to statistical analysis revealing underlying patterns in a collection of data, neural networks locate consistent patterns in a collection of data, based on predetermined criteria.

Suitable pattern recognition algorithms include, but are not limited to, principal component analysis (PCA), Fisher linear discriminant analysis (FLDA), soft independent modeling of class analogy (SIMCA), K-nearest neighbors (KNN), neural networks, genetic algorithms, fuzzy logic, and other pattern recognition algorithms. In some embodiments, the Fisher linear discriminant analysis (FLDA) and canonical discriminant analysis (CDA) as well as combinations thereof are used to compare the output signature and the available data from the database.

In other embodiments, principal component analysis is used. Principal component analysis (PCA) involves a mathematical technique that transforms a number of correlated variables into a smaller number of uncorrelated variables. The smaller number of uncorrelated variables is known as principal components. The first principal component or eigenvector accounts for as much of the variability in the data as possible, and each succeeding component accounts for as much of the remaining variability as possible. The main objective of PCA is to reduce the dimensionality of the data set and to identify new underlying variables.

In practice, principal component analysis compares the structure of two or more covariance matrices in a hierarchical fashion. For instance, one matrix might be identical to another except that each element of the matrix is multiplied by a single constant. The matrices are thus proportional to one another. More particularly, the matrices share identical eigenvectors (or principal components), but their eigenvalues differ by a constant. Another relationship between matrices is that they share principal components in common, but their eigenvalues differ. The mathematical technique used in principal component analysis is called eigenanalysis. The eigenvector associated with the largest eigenvalue has the same direction as the first principal component The eigenvector associated with the second largest eigenvalue determines the direction of the second principal component. The sum of the eigenvalues equals the trace of the square matrix and the maximum number of eigenvectors equals the number of rows of this matrix.

Applications

The present invention provides a method to detect volatile compounds in a sample, comprising exposing the sensors of the electronic nose device to a sample and using pattern recognition algorithms in order to identify and possibly quantify the components of the sample.

In one embodiment, the present invention is used to detect minute concentrations of volatile organic compounds. In a currently preferred embodiment, the electronic devices of the present invention provide detection of volatile organic compounds at levels as low as parts per billion (ppb) or less.

According to one embodiment, the Si NW sensors are in a field effect transistor configuration. These field effect transistors are typically used for sensing chemical processes, and are thus known as CHEMFETs. There are many different varieties of CHEMFETS, most of which are based on a common principle, namely the presence of molecules or ions affect the potential of the conducting field effect transistor channel either by directly influencing the gate potential (e.g., for a catalytically active metal gate) or by changing the potential distribution between a "reference electrode gate" and the semiconductor. Since infinitesimal chemical perturbations can result in large electrical response, Si NW sensors are sensitive to, and can be used to detect, minute concentrations of chemicals. Without being bound by any theory or mechanism of action, the Si NW sensors used along with a reference gate and an ideal polar layer, induce a significant field in the channel. This field ensues due to the overall potential difference between the ground and reference electrodes. Thus, the field is induced to compensate for the potential drop.

According to other embodiments, chemical sensing devices can be produced using Si NW field effect transistors with no reference electrode. Such devices have generally been referred to as molecularly controlled semiconductor resistors (MOCSERs). In MOCSERs, the traditional gating electrode is either present at the back, with a molecular layer adsorbed directly on the semiconductor, or is replaced altogether by a molecular layer adsorbed on a (typically ultra-thin) dielectric. Without being bound by any theory or mechanism of action, in either one of said configurations, binding of molecules from the gas or liquid phase to the "chemical sensing molecules", possibly changes the potential in the conducting channel. Consequently, the current between source and drain is modified and the device serves as a sensor. Such devices possess high chemical sensitivity.

In one embodiment, the present invention is used to diagnose a disease in a subject, by detecting biomarkers indicative of the disease in the headspace of a container of a bodily fluid, such as, but not limited to, serum, urine, feces, vaginal discharge, sperm, saliva etc. The system can detect volatile organic compounds in breath that is directly exhaled by the subject towards the device, without a need for sample pre-concentration. Other possibilities include exhaling into a balloon and then exposing the collected breath to the electronic nose device.

In a preferred embodiment, the method described herein is used to diagnose cancer. GC-MS studies have shown that volatile $C_4$-$C_{20}$ alkanes and certain monomethylated alkanes and benzene derivatives appear to be elevated in instances of cancer. The compounds of interest are generally found at 1-20 ppb in healthy human breath, but can be seen in distinctive mixture compositions at elevated levels from 10-100 ppb in the breath of diseased patients. The levels of volatile organic compounds are elevated even at the early stages of the disease since they reflect a change in the human body chemistry. Also, biomarkers of a specific disease (e.g., lung cancer) have distinctive mixture compositions/patterns in comparison to other diseases (e.g., breast cancer).

In one embodiment, the present invention relates to the diagnosis of cancer using the electronic nose device disclosed herein. The term cancer refers to a disorder in which a population of cells has become, in varying degrees, unresponsive to the control mechanisms that normally govern proliferation and differentiation. Cancer refers to various types of malignant neoplasms and tumors, including metastasis to different sites. Non-limiting examples of cancers which can be detected by the electronic devices of the present invention are brain, ovarian, colon, prostate, kidney, bladder, breast, lung, oral, and skin cancers. Specific examples of cancers are: adenocarcinoma, adrenal gland tumor, ameloblastoma, anaplastic tumor, anaplastic carcinoma of the thyroid cell, angiofibroma, angioma, angiosarcoma, apudoma, argentaffinoma, arrhenoblastoma, ascites tumor cell, ascitic tumor, astroblastoma, astrocytoma, ataxia-telangiectasia, atrial myxoma, basal cell carcinoma, benign tumor, bone cancer, bone tumor, brainstem glioma, brain tumor, breast cancer, vaginal tumor, Burkitt's lymphoma, carcinoma, cerebellar astrocytoma, cervical cancer, cherry angioma, cholangiocarcinoma, a cholangioma, chondroblastoma, chondroma, chondrosarcoma, chorioblastoma, choriocarcinoma, larynx cancer, colon cancer, common acute lymphoblastic leukaemia, craniopharyngioma, cystocarcinoma, cystofibroma, cystoma, cytoma, ductal carcinoma in situ, ductal papilloma, dysgerminoma, encephaloma, endometrial carcinoma, endothelioma, ependymoma, epithelioma, erythroleukaemia, Ewing's sarcoma, extra nodal lymphoma, feline sarcoma, fibroadenoma, fibrosarcoma, follicular cancer of the thyroid, ganglioglioma, gastrinoma, glioblastoma multiforme, glioma, gonadoblastoma, haemangioblastoma, haemangioendothelioblastoma, haemangioendothelioma, haemangiopericytoma, haematolymphangioma, haemocytoblastoma, haemocytoma, hairy cell leukaemia, hamartoma, hepatocarcinoma, hepatocellular carcinoma, hepatoma, histoma, Hodgkin's disease, hypernephroma, infiltrating cancer, infiltrating ductal cell carcinoma, insulinoma, juvenile angiofibroma, Kaposi sarcoma, kidney tumour, large cell lymphoma, leukemia, chronic leukemia, acute leukemia, lipoma, liver cancer, liver metastases, Lucke carcinoma, lymphadenoma, lymphangioma, lymphocytic leukaemia, lymphocytic lymphoma, lymphocytoma, lymphoedema, lymphoma, lung cancer, malignant mesothelioma, malignant teratoma, mastocytoma, medulloblastoma, melanoma, meningioma, mesothelioma, metastatic cancer, Morton's neuroma, multiple myeloma, myeloblastoma, myeloid leukemia, myelolipoma, myeloma, myoblastoma, myxoma, nasopharyngeal carcinoma, nephroblastoma, neuroblastoma, neurofibroma, neurofibromatosis, neuroglioma, neuroma, non-Hodgkin's lymphoma, oligodendroglioma, optic glioma, osteochondroma, osteogenic sarcoma, osteosarcoma, ovarian cancer, Paget's disease of the nipple, pancoast tumor, pancreatic cancer, phaeochromocytoma, pheochromocytoma, plasmacytoma, primary brain tumor, progonoma, prolactinoma, renal cell carcinoma, retinoblastoma, rhabdomyo sarcoma, rhabdosarcoma, solid tumor, sarcoma, secondary tumor, seminoma, skin cancer, small cell carcinoma, squamous cell carcinoma, strawberry haemangioma, T-cell lymphoma, teratoma, testicular cancer, thymoma, trophoblastic tumor, tumourigenic, vestibular schwannoma, Wilm's tumor, or a combination thereof.

The system of the present invention can further help diagnose other medical disorders including, but not limited to, acute asthma, hepatic coma, rheumatoid arthritis, schizophrenia, ketosis, cardiopulmonary disease, uremia, diabetes mellitus, dysgeusia/dysosmia, cystinuria, cirrhosis, histidinemia, tyrosinemia, halitosis, and phenylketonuria.

The present invention also relates to non-oxidized functionalized Si NW sensors in which the functional group is tailor-made to allow for specific identification of compounds selected from vapors of volatile organic compounds. The technology of the present invention provides fine tuning of the devices through modifying the functional groups attached to the Si NW to high density functionalities which allow better signal/noise ratios.

Due to the miniaturized dimensions of the electronic nose device (in the range of 10-100 nanometers to a few micrometers), these devices could be installed in many electronic apparatuses. For example, these devices could be integrated into a watch or cellular phone, to provide a warning system for the initiation of an infection or other disease in the body of an individual.

The system of the present invention can be used in many other different applications wherein the detection of volatile organic compounds is feasible. These applications include, but are not limited to, environmental toxicology and remediation, medicine, materials quality control, food and agricultural products monitoring, heavy industrial manufacturing (automotive, aircraft, etc.), such as ambient air monitoring, worker protection, emissions control, and product quality testing; oil/gas petrochemical applications, such as combustible gas detection, $H_2S$ monitoring, hazardous leak detection and identification; hazardous spill identification, enclosed space surveying, utility and power applications, such as emissions monitoring and transformer fault detection; food/beverage/agriculture applications, such as freshness detection, fruit ripening control, fermentation process monitoring and control, flavor composition and identification, product quality and identification, and refrigerant and fumigant detection.

Additional applications include, but are not limited to, cosmetic/perfume applications, such as fragrance formulation, product quality testing, and fingerprinting; chemical/plastics/pharmaceuticals applications, such as fugitive emission identification, leak detection, solvent recovery effectiveness, perimeter monitoring, and product quality testing; hazardous waste site applications, such as fugitive emission detection and identification, leak detection and identification, transportation applications, such as hazardous spill monitoring, refueling operations, shipping container inspection, and diesel/gasoline/aviation fuel identification; building/residential applications, such as natural gas detection, formaldehyde detection, smoke detection, automatic ventilation control (cooking, smoking, etc.), and air intake monitoring; hospital/medical applications, such as anesthesia and sterilization gas detection, infectious disease detection, breath, wound and bodily fluids analysis, and telesurgery.

The principles of the present invention are demonstrated by means of the following non-limitative examples.

EXAMPLES

Example 1

Synthesis of the Silicon Nanowires (Si NWs)

Figure 3:
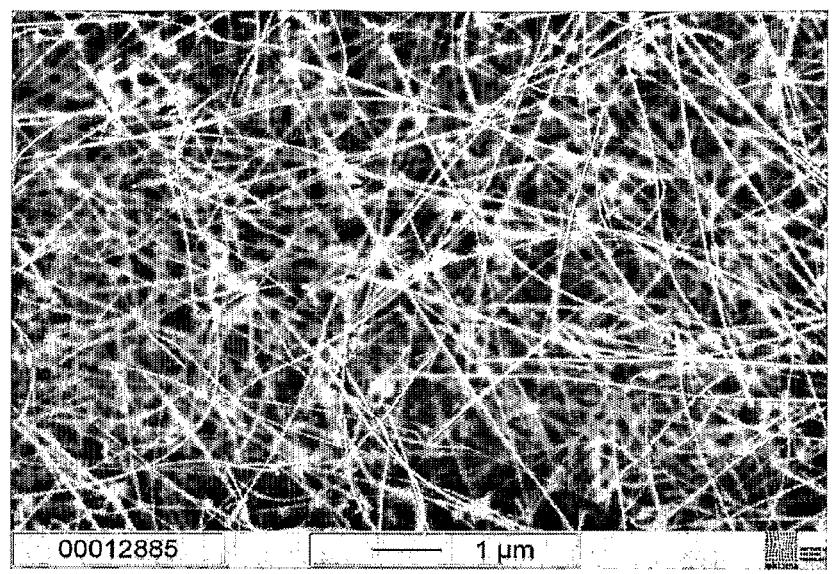
FIG. 3 is a Scanning Electron Micrograph of "as-grown" Si NWs.
Figure 4:
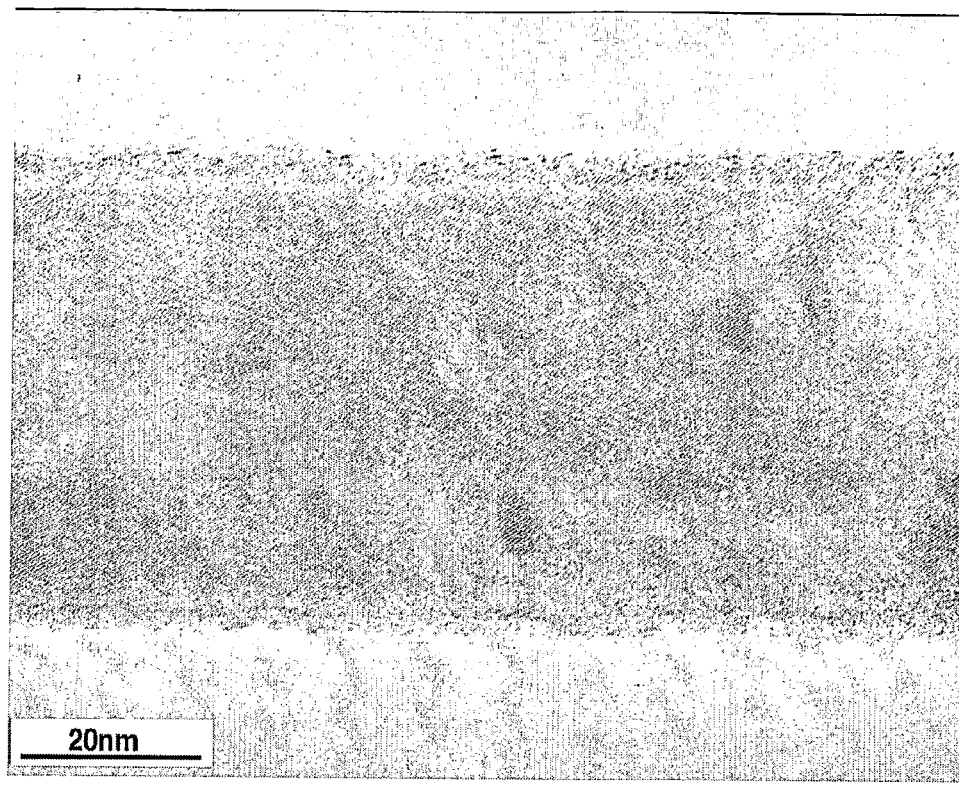
FIG. 4 is a high resolution Transmission Electron Micrograph of an individual Si NW coated with a thin native oxide layer.

Si NWs were prepared by the vapor-liquid-solid (VLS) growth method using chemical vapor deposition (CVD) with silane on Si(111) substrates. Si substrates were etched in diluted HF to remove the native oxide following by sputtering of a 2 nm thick Au film on the substrate. The sample was transferred into the CVD chamber, and annealed at ~580° C. with a pressure of ~5×10$^{-7}$ mbar for 10 minutes. The temperature was then dropped to ~520° C. and a mixture of 5-10 sccm Ar and 5 sccm $SiH_4$ was introduced for 20 minutes at a pressure of 0.5-2 mbar to obtained undoped Si NWs. FIG. 3 shows a typical Scanning Electron Micrograph of Si NWs grown from gold (Au) seeds. FIG. 4 shows Transmission Electron Micrograph of the Si NWs in which the majority of the NWs exhibit smooth 50±10 nm diameter Si cores coated with 3-4 nm $SiO_2$, having lengths in the range of 2-4 μm.

Doped Si NWs were prepared by the vapor-liquid-solid (VLS) growth technique under gas ratios of 10 sccm He, 5 sccm $SiH_4$, and 0.02 sccm $B_2H_6$ (2% in He), yielding p-type Si NWs doped with Boron. TEM characterization indicated that these NWs are essentially smooth having a diameter of 52±8 nm. The surface of the Si NW was covered with native oxide and minute amounts of gold.

Example 2

Alkylation of Si Nanowires (Si NWs) through Si—C bond

Functionalization of the Si NWs of the present invention was performed using a two-step chlorination/alkylation route. Prior to any chemical treatment, each sample was cleaned using a nitrogen ($N_{2(g)}$) flow. Hydrogen-terminated Si NWs were then prepared by etching the amorphous $SiO_2$ coating. This was done through exposing the Si NWs to buffered HF solution (pH=5) for 60 seconds followed by exposure to $NH_4F$ for 30 seconds. It is noteworthy that longer exposures to HF and/or $NH_4F$ results in fluorination of the sample thus interfering with the alkylation process. The sample was then removed and rinsed in water for <10 seconds per each side to limit oxidation, and dried in $N_{2(g)}$ flow for 10 seconds. The sample was transferred into a glove-box with $N_{2(g)}$-atmosphere for functionalization.

Figure 5A:
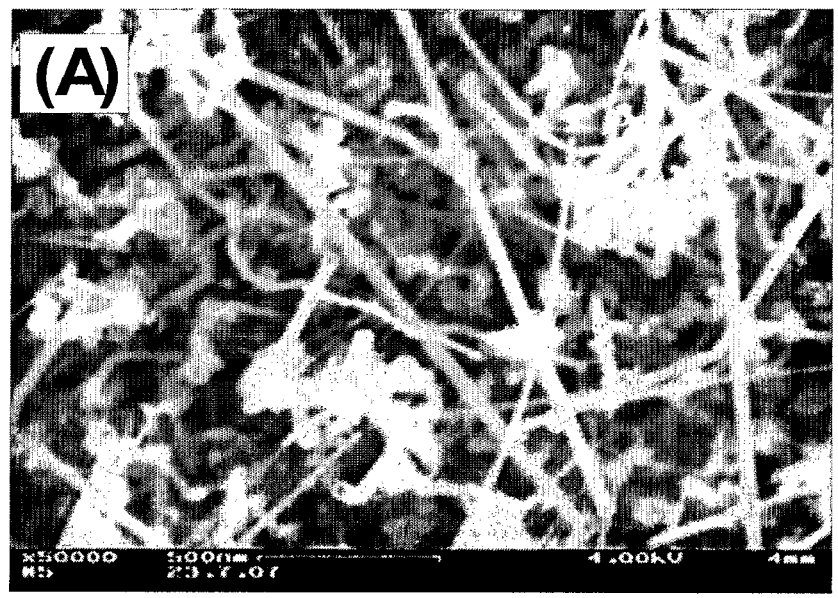
FIG. 5(A-B) are high resolution-Scanning Electron Micrographs of Si NWs before (5A), and after (5B) alkylation for 24 hours. The Si NWs are about 2-4 µm in length and about 50 nm in diameter.
Figure 5B:
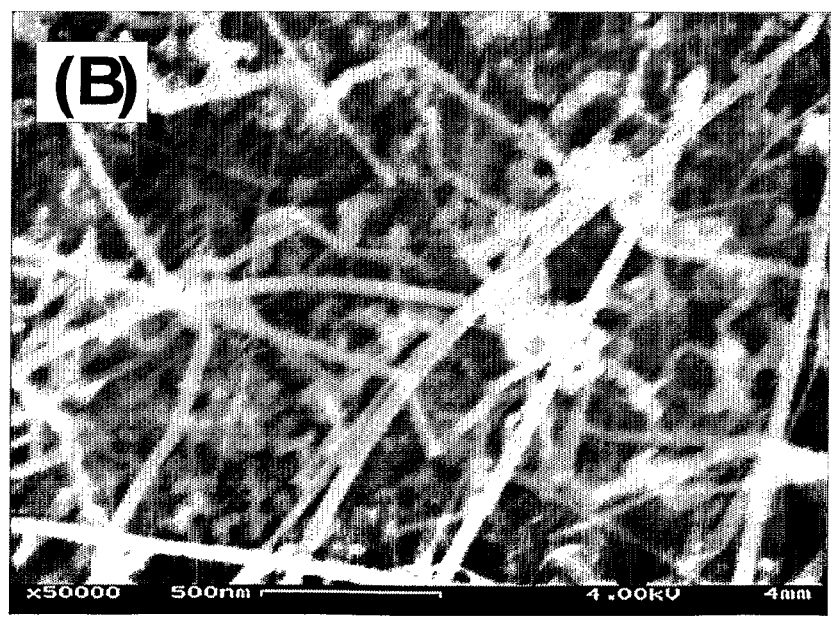

Functionalization was preformed by immersing the sample into a saturated solution of $PCl_5$ in $C_6H_5Cl$ (0.65M) that contained a few grains of $C_6H_5OOC_6H_5$ to act as a radical initiator (Hassler and Koell, *J. Organometal. Chem.* 1995, 487, 223). The reaction solution was heated to 90-100° C. for 5 minutes. The sample was then removed from the reaction solution and rinsed in tetrahydrofuran (THF) followed by a methanol (CH$_3$OH) rinse and drying under a stream of N$_{2(g)}$. Additionally, several samples were further rinsed with 1,1,1-trichloroethane (TCE) before drying under N$_{2(g)}$ flow. The chlorine-terminated Si NWs were alkylated by immersion in 0.5M alkyl Grignard in THF (RMgCl: where R represents an alkyl chain with 1-7 carbon atoms). The reaction was performed for 30-250 minutes at 80° C. Excess THF was added to all reaction solutions for solvent replacement. At the end of the reaction, the sample was removed from the reaction solution and was then rinsed in THF, methanol, and occasionally TCE. The sample was then dried under a stream of N$_{2(g)}$. Though the PCl$_5$ is known to extremely damage and break the Si NWs in exposure of 10 minutes or more, High resolution Scanning Electron Micrographs (HRSEM, Zeiss Leo 982, Germany; operated at 4 KV) confirmed that the alkylation process used herein did not damage or break the Si NWs which remained with the same dimensions as prior to the alkylation (FIGS. 5A-B).

Example 3

The Kinetics of Formation of Functionalized Si NWs

Figure 6:
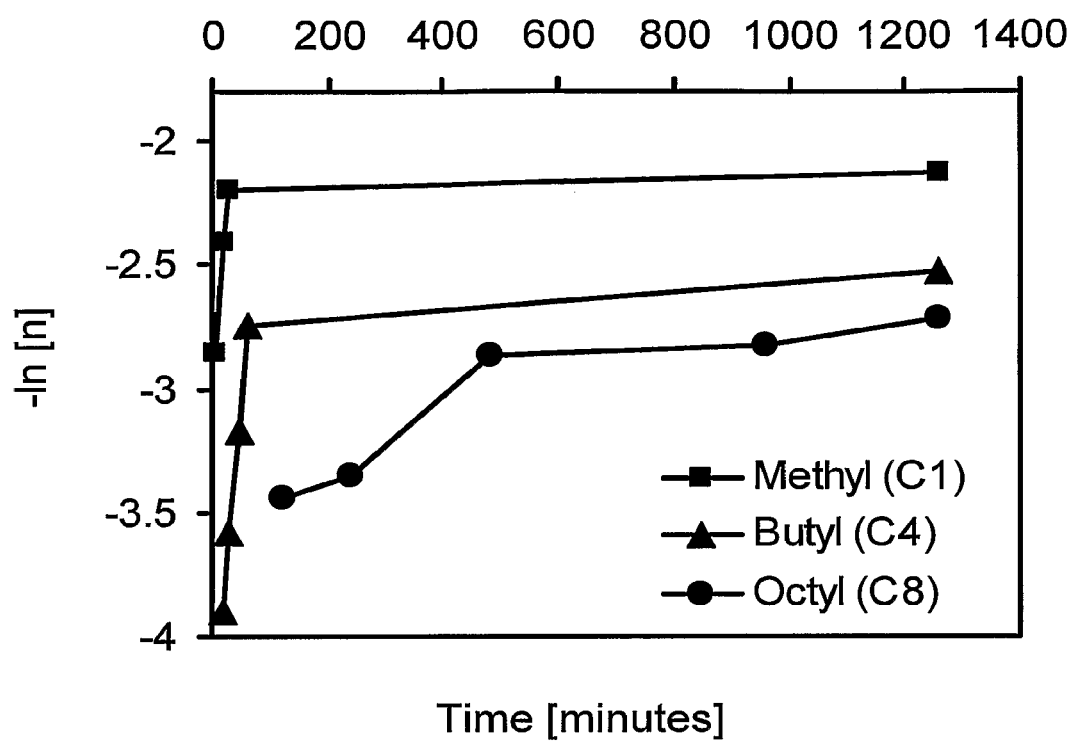
FIG. 6 is a pseudo-first-order-fitting of the kinetics of formation of functionalized Si NWs.
Figure 7A:
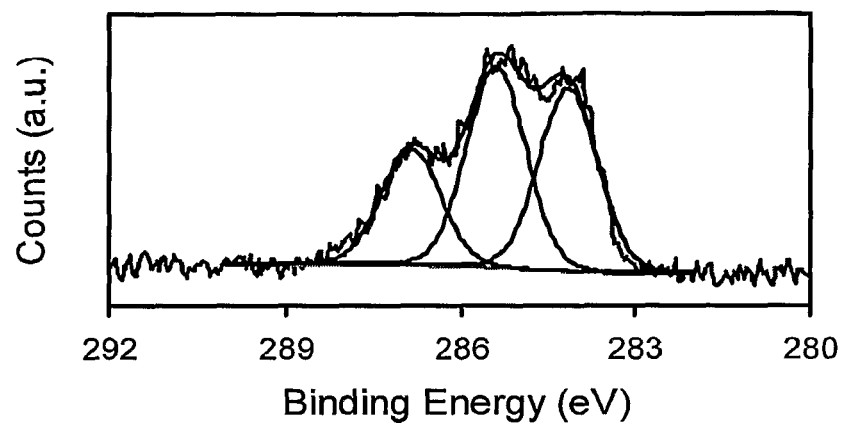
FIG. 7(A-I) are XPS data of C 1 s region, showing C—Si (284.1±0.1 eV), C—C (285.2±0.1 eV) and C—O (286.7±0.1 eV) peaks of freshly-prepared samples of non-oxidized Si NWs functionalized with (7A) methyl, (7B) ethyl, (7C) propyl, (7D) butyl, (7E) pentyl, (7F) hexyl, (7G) octyl, (7H) decyl, and (7I) undecyl.
Figure 7B:
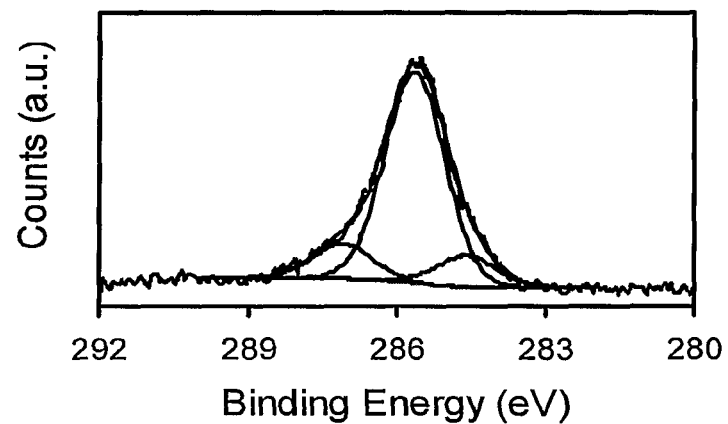
Figure 7C:
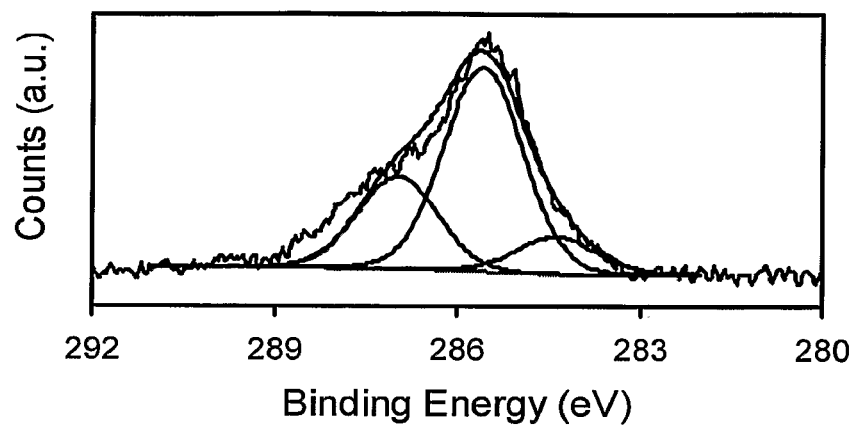
Figure 7D:
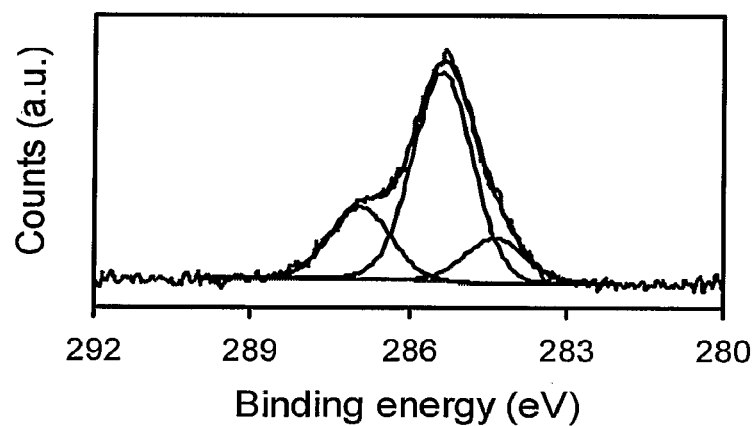
Figure 7E:
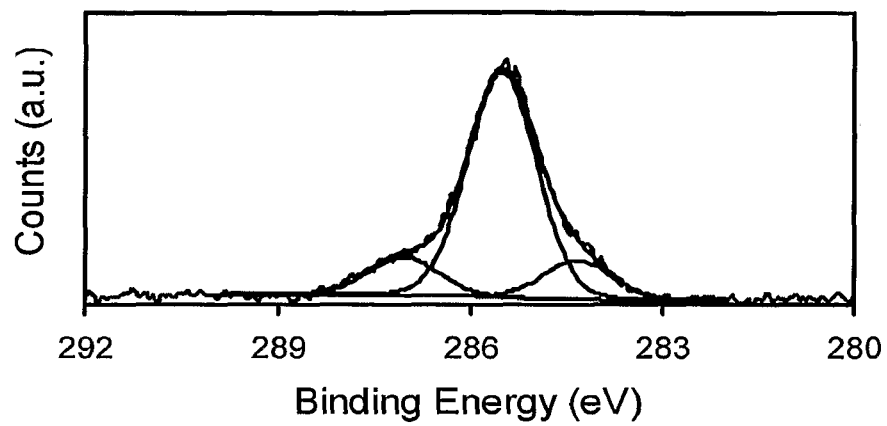
Figure 7F:
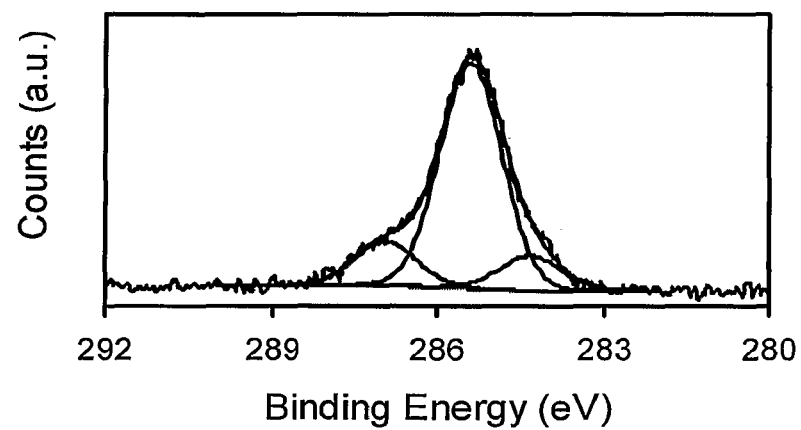
Figure 7G:
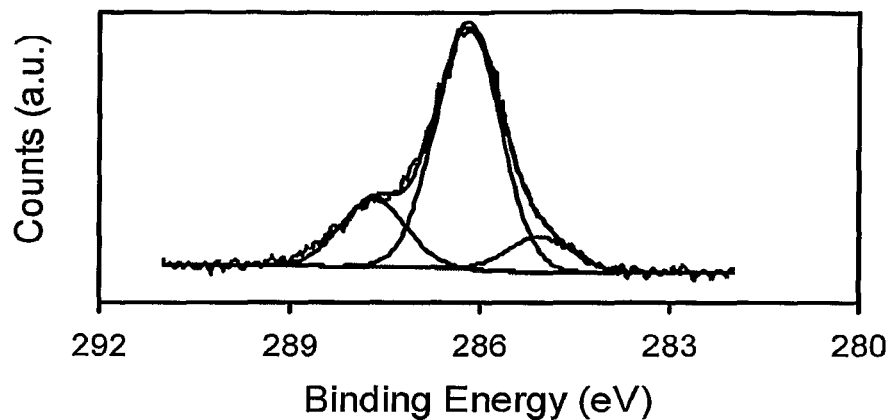
Figure 7H:
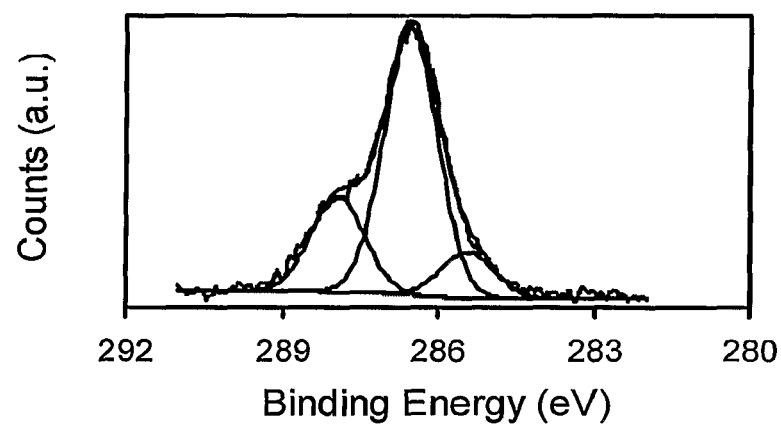
Figure 7I:
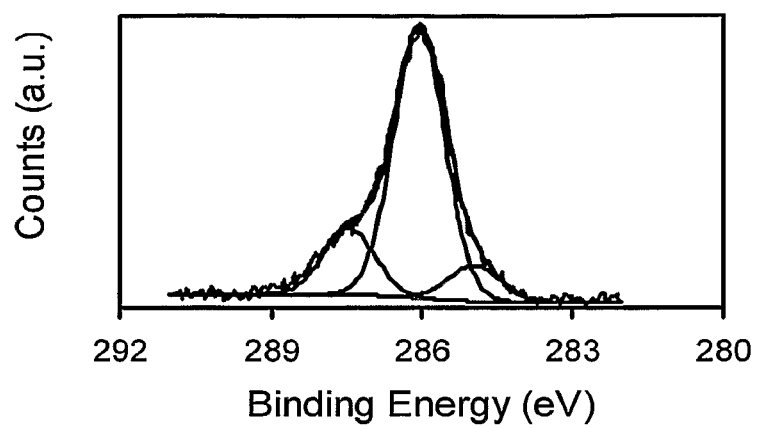
Figure 8A:
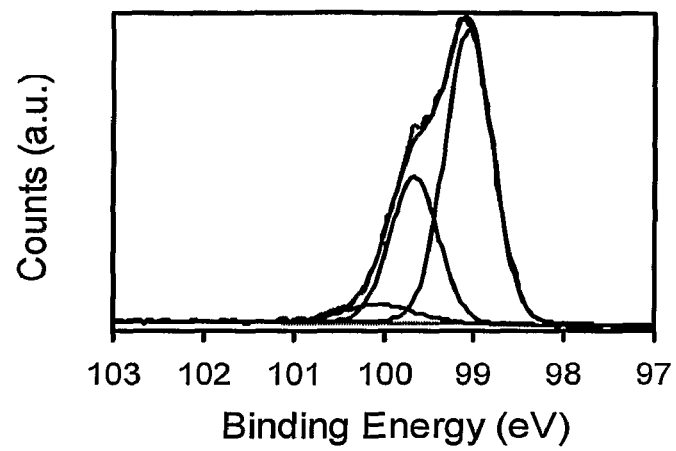
FIG. 8(A-H) are XPS data of Si 2p region (8A, 8C, 8E, and 8G) and C is region (8B, 8D, 8F, and 8H). The non-oxidized Si NWs were functionalized with the following functional groups: (8A and 8B) $CH_3$—Si, (8C and 8D) $CH_3$—$CH_2$—$CH_2$—Si, (8E and 8F) $CH_3$—CH=CH—Si, and (8G and 8H) $CH_3$—C≡C—Si.
Figure 8B:
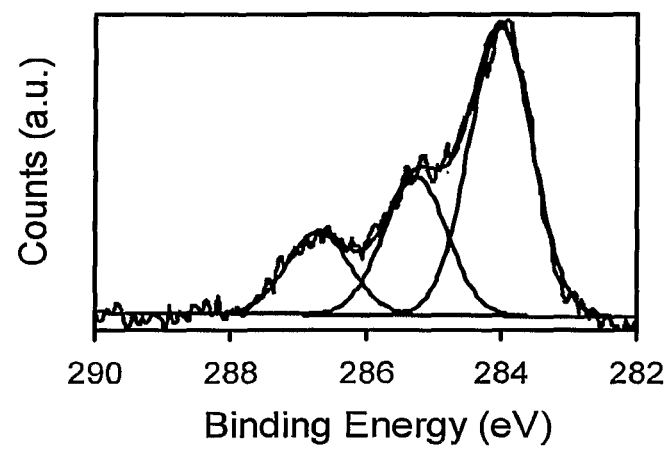
Figure 8C:
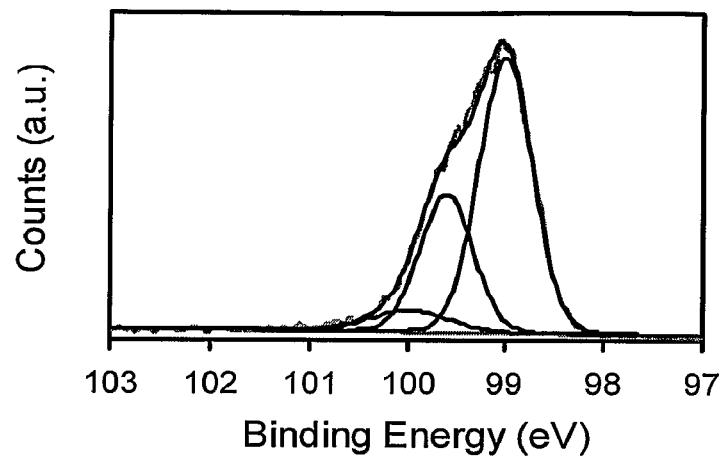
Figure 8D:
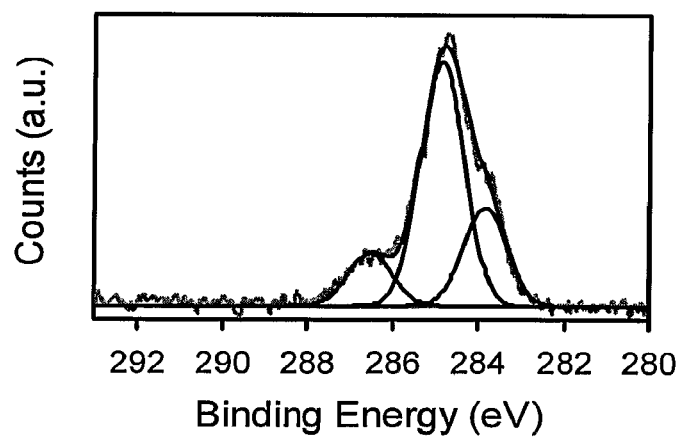
Figure 8E:
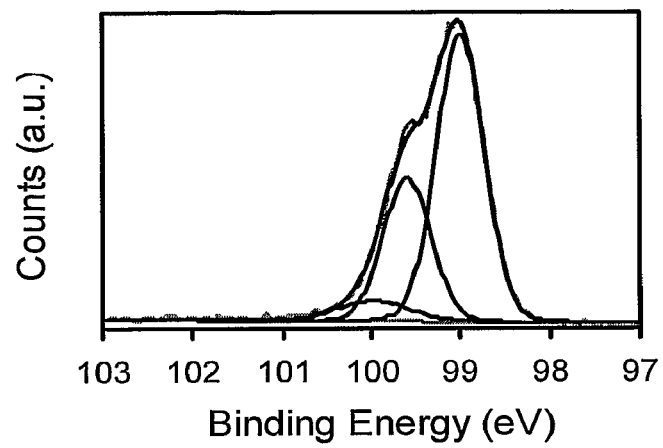
Figure 8F:
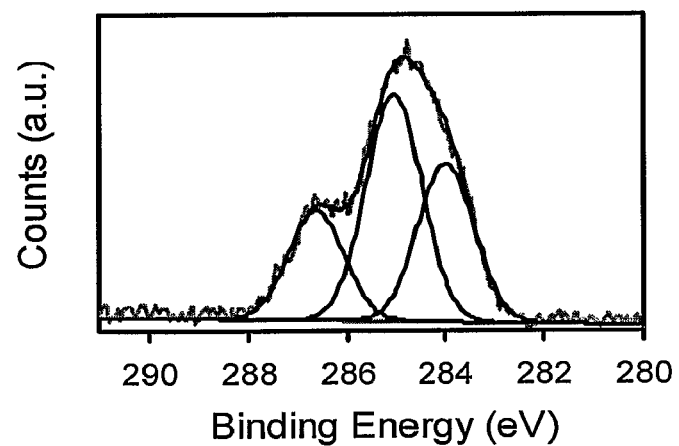
Figure 8G:
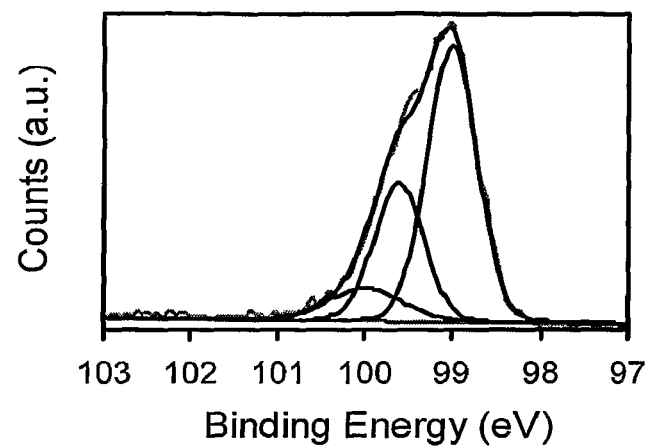
Figure 8H:
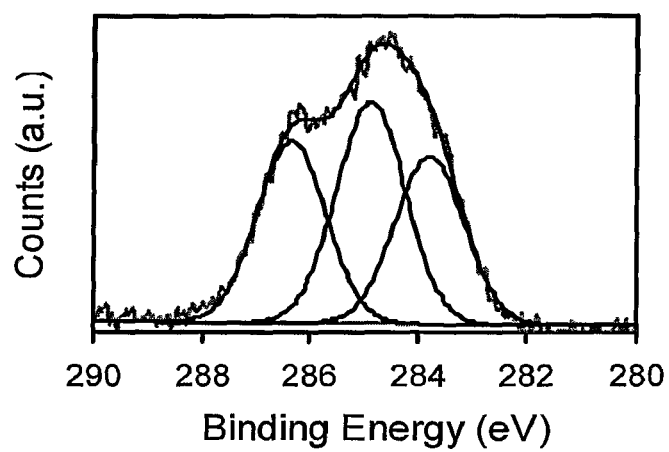

The coverage of Si NW surfaces with various alkyl chains was plotted as a function of time. FIG. 6 shows a semi-logarithmic plot from which the pseudo-first-order rate constant of the reaction was calculated. Two distinct regions are observed in the curves: at short time intervals an accelerated rate is obtained (corresponds to a Kp1 slope) and at longer time intervals mildly increased rate is obtained (corresponds to a Kp2 slope). Without being bound by any theory or mechanism of action, the increased rate is attributed to the lack of steric hindrance between adjacent alkyl chains. This result is compatible with the kinetics of a pseudo-first-order reaction.

The kinetics of pseudo first order (ln [n]=–K$_{p1}$*t) is detected for up to about 90% of a full coverage of the Si NWs followed by a decrease in rate thereafter. The two main regions in the alkylation process of the NWs are from zero to Γsat, and from Γsat to longer alkylation times (mostly 24 hours). Over 90% of the Si NW surfaces were covered with the alkyl molecules after short immersion time. Additionally, Kp1 was found to decrease as the alkyl chain increases, namely the longer the molecular chains the longer the time required for alkylation. In contrast, Kp2 was found essentially unaffected by the length of the alkyl chain indicating a "zero-order" reaction. Table 1 summarizes the saturation level of the adsorption curve (Γsat values) for different alkyl functional groups along with the related $(C_{Si}/Si)_{alkyl}/(C_{Si}/Si)_{methyl}$ ratios. The ethylated surfaces showed a $(C_{Si}/Si)_{ethyl}/(C_{Si}/Si)_{methyl}$ value of 70±5%, indicating that ethyl (C$_2$) groups can be packed at a very high density without major steric hindrance effects. Propyl (C$_3$), butyl (C$_4$), pentyl (C$_5$), hexyl (C$_6$), octyl (C$_8$), decyl (C$_{10}$) and undecyl (C$_{11}$) produced 56±5%, 49±5%, 50±10%, 56±6%, 54±5%, 77±04%, and 57±02% coverage, respectively. The percentages of coverage are substantially higher than the coverage of the same functional groups on 2D Si (100) surfaces (Table 1). Furthermore, the time required to achieve maximum coverage of the molecules on Si NWs (where the molecules cover 50-100% of the atop Si sites) is 4 to 30 times shorter than that required for the 2D surfaces (where the molecules cover <55% of the atop Si sites). Without being bound by any theory or mechanism of action, these differences could be attributed to surface energy, activation energy and steric hindrance effects between the adsorbed molecules wherein an increase in the length of the alkyl chain increases the van der Waals diameter to >4.5-5.0 Å, significantly larger than the inter-nuclear distance between adjacent Si atoms (3.8 Å). In other words, Kp1 decreases as the alkyl chain length increases. For example, Kp1 of methyl group (2.64×10$^{-2}$) is 38 times larger than Kp1 of decyl group (7.0×10$^{-4}$). An additional factor which influences the decay in the rate constants is the accessibility of the Si atoms to nucleophilic carbon attack. Thus, the curvature of the Si NWs reduces the steric hindrance effect between the molecules allowing a higher surface coverage and a shorter alkylation time. Therefore, decreasing the diameter of the Si NWs is expected to allow full-passivation of longer alkyl chains (>C$_6$).

Without being bound by any theory or mechanism of action, at high coverage, a significant fraction of the available surface sites are surrounded by occupied sites and cannot be accessed by a propagating random walk, At this stage, the inter-steric-effect is more dominant than the nucleophilic attack effect and the kinetic behavior is no longer controlled by the nucleophile concentration thus switching to "zero-order" kinetics.

TABLE 1

Summary of the XPS results for C$_1$-C$_{11}$ chains bonded to Si NW and 2D Si surfaces via Si—C bond

| Alkyl | Γ$_{sat}$[a] [min] | C$_{Si}$/Si$_{2p}$ ratio for Si NW | Max. coverage[b] on Si NW | C$_{Si}$/Si$_{2p}$ ratio for Si 2D(100) | Max. coverage[b] on 2D Si (100) |
|---|---|---|---|---|---|
| Methyl (C$_1$) | 20 ± 2 | 0.135 ± 0.001 | — | 0.135 ± 0.001 | — |
| Ethyl (C$_2$) | 50 ± 10 | 0.093 ± 0.003 | 70 ± 5% | 0.090 ± 0.02 | 60 ± 20% |
| Propyl (C$_3$) | 60 ± 10 | 0.075 ± 0.006 | 56 ± 5% | 0.048 ± 0.002 | 35 ± 2% |
| Butyl (C$_4$) | 65 ± 10 | 0.066 ± 0.004 | 49 ± 5% | 0.049 ± 0.006 | 35 ± 4% |
| Pentyl (C$_5$) | 90 ± 10 | 0.068 ± 0.012 | 50 ± 10% | 0.051 ± 0.003 | 35 ± 5% |
| Hexyl (C$_6$) | 120 ± 10 | 0.076 ± 0.009 | 56 ± 6% | 0.055 ± 0.004 | 40 ± 4% |
| Octyl (C$_8$) | 450 ± 20 | 0.073 ± 0.002 | 54 ± 5% | 0.056 ± 0.002 | 40 ± 10% |
| Decyl (C$_{10}$) | 1000 ± 50 | 0.104 ± 0.003 | 77 ± 04% | 0.058 ± 0.012 | 40 ± 10% |
| Undecyl (C$_{11}$) | 1000 ± 50 | 0.077 ± 0.003 | 57 ± 02% | 0.029 ± 0.006 | 20 ± 6% |

[a]Γsat is the time required to achieve 92 ± 3% of the saturation level of the adsorption curve.
[b]Coverage is calculated as $(C_{Si}/Si)_{alkyl}/(C_{Si}/Si)_{methyl}$.

Example 4

Characterization of the Functionalized Si NWs

Transmission electron microscopy (TEM) images of freshly-prepared functionalized Si NW samples showed a core diameter similar to the $SiO_2$-coated Si NWs. X-ray Photoelectron Spectroscopy (XPS) data from the carbon 1 s (C 1s) emission region of the alkyl-functionalized Si NWs, was fitted to three peaks, namely C—Si at 284.1±0.1 eV, C—C at 285.2±0.1 eV, and C—O at 286.7±0.1 eV. FIGS. 7A-7I show representative C 1 s region XPS data and fits of non-oxidized Si NWs functionalized with (A) methyl at 20 minutes alkylation, (B) ethyl at 80 minutes alkylation, (C) propyl at 120 minutes alkylation, (D) butyl at 160 minutes alkylation, (E) pentyl at 160 minutes alkylation, (F) hexyl at 240 minutes alkylation, (G) octyl at 450 minutes alkylation, (H) decyl at 1000 minutes alkylation, and (I) undecyl at 1000 minutes alkylation. The peaks were typically adjusted to produce fits that minimized the difference between the full widths at half-maximum (FWHM). Peak centers were allowed to float, while the center-to-center distances were fixed at 1.1 eV between the C—Si and the C—C emissions, and at 2.6 eV between the C—O and the C—Si emissions. The integrated area under each carbon peak was normalized to the integrated area under the silicon 2p (Si 2p) peaks for each sample scan. The ratio of the C—Si to the normalized area for the Si 2p peak ($C_{Si}$/Si) was then compared between different alkylated surfaces. Si NWs functionalized with methyl group were used as a reference surface for the other alkylated Si NW surfaces. The surface coverage for each alkyl group is thus reported as $(C_{Si}/Si)_{alkyl}/(C_{Si}/Si)_{methyl}$. XPS survey spectra of freshly-prepared alkyl-functionalized Si NWs showed Si, C, O and Au with little (less than 1%) or no detectable Mg or Cl peaks. No oxide peaks in the XPS spectra were observed on these freshly-prepared alkylated surfaces.

Occasionally, a small oxygen signal was observed at 532 eV (O 1s). This signal was assigned to adventitious adsorbed hydrocarbons having oxygen bonded to carbon (286 eV) as a result of wet chemical etching and subsequent exposure to air. No $SiO_2$ was observed in the high resolution Si 2p XPS scans as well as in energy dispersive spectrometry (EDS) measurements, further supporting the origin of the O 1s to be due to adventitious O on the surface. The lack of a fluorine 1 s (F 1s) signal in the XPS survey data, which would have appeared at 686 eV binding energy, confirmed that the $NH_4F_{(aq)}$-etched silicon surface was not functionalized with Si—F species.

The silicon nanowires surfaces of the present invention have been functionalized with various saturated and unsaturated organic molecules having single, double and triple bonds, by the two step chlorination/alkylation reaction (Grignard reagent).

FIGS. 8A-8H show high resolution XPS scans of Si 2p and C 1 s regions of propyl, propenyl, propynyl and methyl-functionalized silicon nanowires surfaces ($CH_3$—$CH_2$—$CH_2$—Si, $CH_3$—CH=CH—Si, $CH_3$—C≡C—Si, $CH_3$—Si, respectively). In Si 2p spectrum the ratios of Si $2p_{3/2}$ and $Si2p_{1/2}$ produce the expected 2:1 area ratio having 0.6 eV energy separation. No $SiO_2$ is detectable after alkylation (FIGS. 8A, 8C, 8E, and 8G). Three peaks were observed at 284±0.1%, 285.2 d 0.1% and 286.6±0.1% eV in C 1 s spectrum (FIGS. 8B, 8D, 8F, and 8H). The peaks at 285.2±0.1% and 286.6±0.1% eV are common to all alkylated and H-terminated Si surfaces, whereas the low binding energy peak at 284±0.1% eV is unique to alkylated Si nanowire surfaces.

The ratio of C—Si/Si 2p peak area provides quantitative information regarding the coverage of Si NWs with the various functional groups. Since methylation has been shown to provide a nearly complete monolayer on the Si (111) surface, Si—$CH_3$ has been used as a reference to calculate coverage percentages of the other functional groups. Si—CH=CH—$CH_3$ surfaces showed a C—Si/Si 2p peak ratio indicating full coverage relative to that of $CH_3$—Si surface. Thus, Si—CH=CH—$CH_3$ can be packed at very high density by using the two step chlorination/alkylation method presented herein. Similarly, C—Si/Si 2p peak ratio for Si—C≡C—$CH_3$ and Si—$CH_2$—$CH_2$—$CH_3$ produced coverage percentages of 97±5% and 60±5%, respectively, in comparison to methyl coverage.

Example 5

Stability of the functionalized Si NWs

Functionalized Si NWs were exposed to ambient conditions for several weeks, to assess their stability. The degree of oxidation was extracted from the ratio between the integrated area under the $SiO_2$ peak (103.5 eV) and the Si 2p peak.

Figure 9:
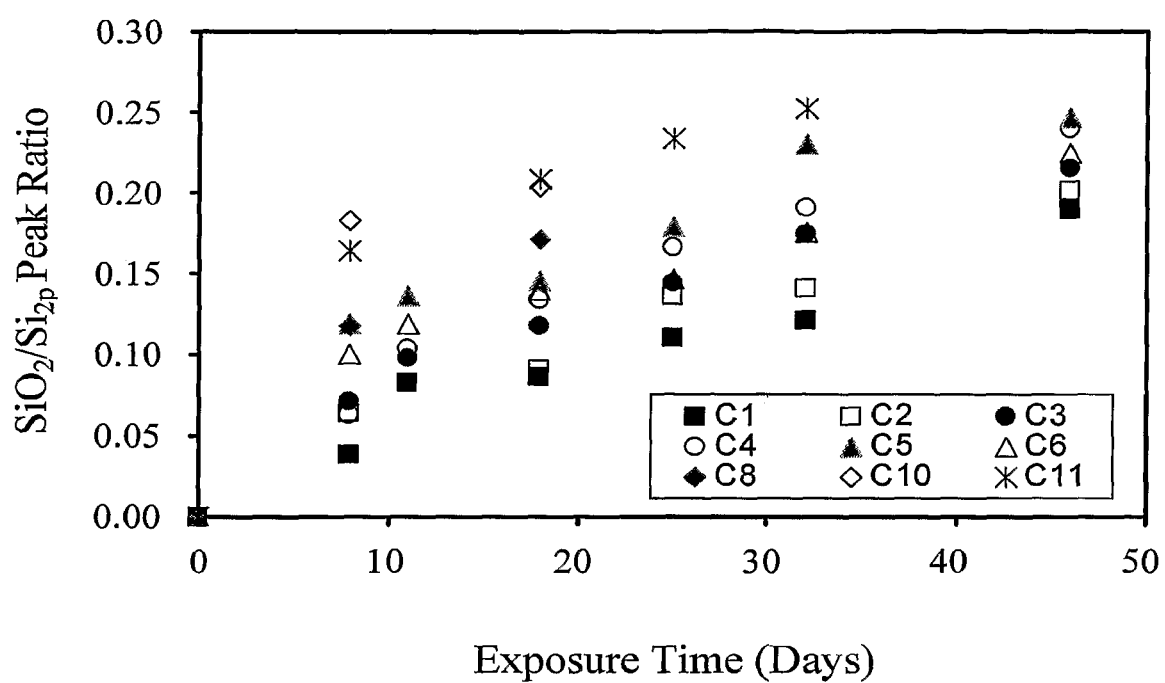
FIG. 9 is the observed oxidation ($SiO_2/Si_{2P}$ peak ratio) at different exposure times to ambient conditions.

The stability of the wires decreased monotonically with the alkyl chain length (Table 2; FIG. 9). Methyl ($C_1$)—functionalized Si NWs that were exposed to air over a period of more than two weeks (336 hours) showed an increased stability (>1.5 times more) than equivalent 2D Si (100) surfaces. Moreover, all molecules showed stability of one monolayer (corresponds to $SiO_2/Si_{2p}$ peak ratio of 0.19-0.26) after 46 days whereas in Si 2D (100) the stability of one monolayer (corresponds to $SiO_2/Si_{2p}$ peak ratio of 0.15-0.18) was obtained after 8 days. Without being bound by any theory or mechanism of action, these differences in stability could be attributed to the higher surface coverage of molecules on Si NWs, than on equivalent 2D Si (100) surfaces.

TABLE 2

Summary of the oxidation $SiO_2/Si_{2p}$ ratio for alkylated Si NWs and 2D Si (100) surfaces at representative exposure times to ambient conditions

| | Exposure time to air | | | |
|---|---|---|---|---|
| Molecule | 0 hr | 24 hr | 48 hr | 336 hr |
| Methyl ($C_1$) - Si NW | 0 | 0 | 0 | 0.04 |
| Methyl ($C_1$) - 2D substrate | 0 | ND | ND | 0.11 |
| Ethyl ($C_2$) - Si NW | 0 | 0 | 0 | 0.03 |
| Ethyl ($C_2$) - 2D substrate | 0 | 0.03 | 0.08 | 0.13 |
| Propyl ($C_3$) - Si NW | 0 | 0.01 | 0.07 | 0.13 |
| Propyl ($C_3$) - 2D substrate | 0 | ND | ND | ND |
| Butyl ($C_4$) - Si NW | 0 | 0.02 | 0.07 | 0.13 |
| Butyl ($C_4$) - 2D substrate | 0 | ND | ND | ND |
| Pentyl ($C_5$) - Si NW | 0 | 0.02 | 0.06 | 0.14 |
| Pentyl ($C_5$) - 2D substrate | 0 | ND | ND | ND |
| Hexyl ($C_6$) - Si NW | 0 | 0.01 | 0.06 | 0.12 |
| Hexyl ($C_6$) - 2D substrate | 0 | 0.04 | 0.08 | 0.18 |

ND = not determined

Example 6

Fabrication of the Si NW Field Effect Transistors

Figure 10:
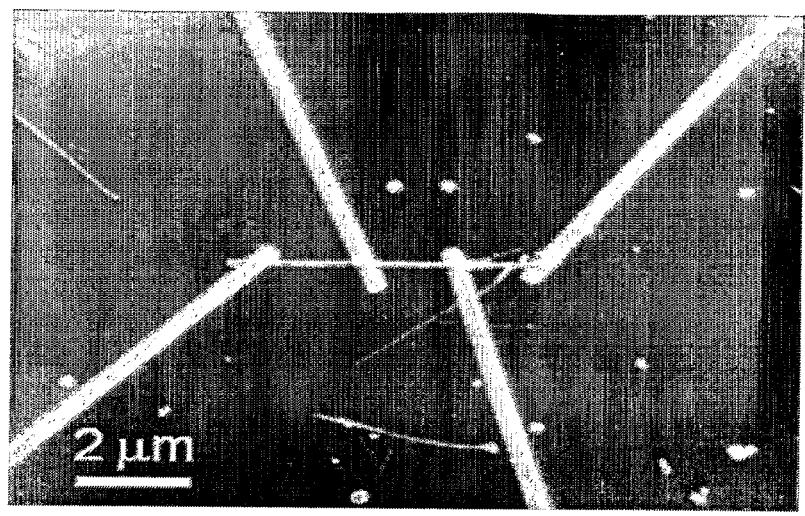
FIG. 10 is a Scanning Electron Micrograph of a Si NW device having four Aluminum (Al) contacts.

Devices were fabricated by depositing four Al electrodes on an individual Si NW on top of a 90 nm thermally oxidized degenerately doped p-type Si (0.001 $\Omega \cdot cm^{-1}$) substrate. The electrodes were mutually separated by 1.70±0.05 μm (FIG. 10). For each Si NW field effect transistor device, the intrinsic conductivity at determined back gate voltage was obtained by the four-point probe method. Particularly, electrical properties collected with the four-point probe method enable the configuration wherein there is no contact resistance between the metallic contacts and the Si NW.

Example 7

Sensing Characterization of Si NW Field Effect Transistors

The developed sensors were placed in a 316-stainless steel chamber with PTFE O-rings. To assess the sensing characteristics of the various Si NWs, current-voltage measurements at determined back gate voltage of each sensor were performed with digital multimeter (model 34411A; Agilent Technologies Ltd.) that is multiplexed with 40-channel armature multiplexer (model 34921A; Agilent Technologies Ltd.). In these measurements, a voltage of –3 V was applied to the degeneratively doped silicon substrate that was coated with 200 nm aluminum, as an ohmic contact. The –3 V back-gate-voltage value was chosen to provide an optimal signal-to-noise ratio of the output signal. Under this value of back gate voltage, four-point probe transport measurements were carried out, at bias range between –5 and +5 V, in steps of 10 mV, with the two inner electrodes serving as voltage probes and the two outer electrodes serving as current probes.

A Labview-controlled automated flow system delivered pulses of simulated mixtures of biomarker vapors at a controlled biomarker vapor pressure optimized to the detector surface area. Dry air was obtained from a house compressed air source, controlled with a 10 L/minute mass flow controller. In a typical experiment, signals of sensor array elements were collected for 70 seconds of clean laboratory air, followed by 80 seconds of analyte vapors in air, followed by another 70 seconds interval of clean air to purge the system. Data analysis of the signals collected from all the sensors in the array was performed using standard principal component analysis.

Example 8

Evaluation of Sensitivity of Si NW Field Effect Transistors

The Si NW FETs of the present invention have improved sensing capabilities in comparison to equivalent $SiO_2$ coated Si NW field effect transistors.

Si NW FET devices were fabricated by integrating an individual Si NW with metallic electrodes that were separated by 500 nm, on top of a 30 nm SiOx that covers degenerately doped Si substrate. FIG. 11 show graphs of the responses of the devices to hexane vapor exposure at concentration of 40 ppb, when applying –3 V back gate voltage, expressed as $\Delta R/R_b$ (where $R_b$ is the baseline resistance of the detector in the absence of analyte, and $\Delta R$ is the baseline-corrected steady-state resistance change upon exposure of the detector to analyte). The graphs demonstrate the improvement of sensing capabilities of the Si NW FET upon, oxide removal and further functionalizing the Si core.

Figure 11A:
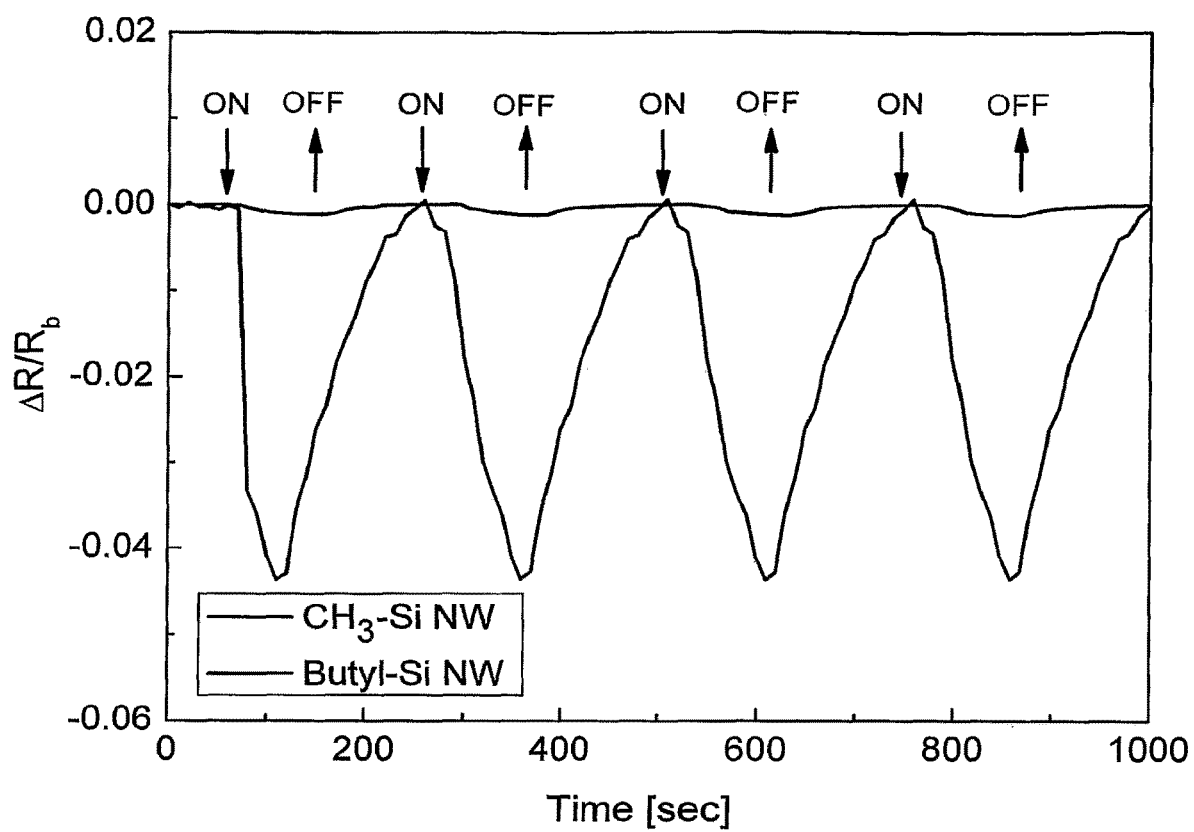
FIG. 11(A-B) are graphs of the responses of the Si NW field effect transistor devices to hexane vapor exposure at low concentrations. (11A) Non-oxidized Si NWs functionalized with $CH_3$ ($CH_3$—Si—NW; upper curve) or butyl (Butyl-Si—NW; lower curve) functional groups; (11B) bare $SiO_2$-coated Si NWs (upper curve), $SiO_2$-coated Si NWs modified with $CH_3$ ($CH_3$—$SiO_2$—Si NW; middle curve), or $SiO_2$-coated Si NWs modified with butyl (Butyl-$SiO_2$—Si NW; lower curve) functional groups.
Figure 11B:
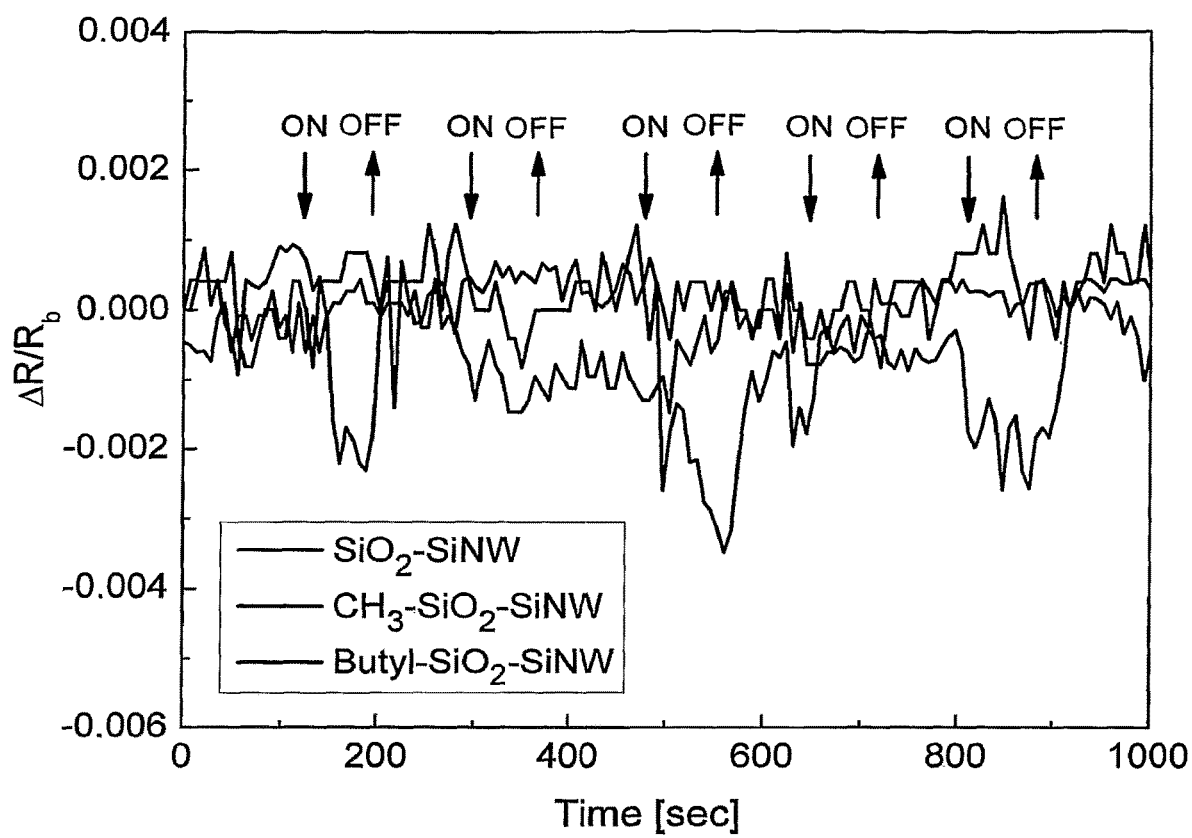

Exposure of Si NW FETs with and without oxide layer (at the interface between the organic layer and Si core) to 40 ppb hexane vapor (as a representative analyte) showed that removing the oxide coating and functionalizing the Si NW core via Si—C bond gives improved, stable, and reproducible responses as well as a high signal-to-noise ratios (FIGS. 11A and 11B). For example, exposure of $SiO_2$-coated Si NW FET to 40 ppb hexane showed almost no significant differences between the responses collected in turn-on/shut-off (ON/OFF) exposure cycles (FIG. 11B; upper curve). Self-assembly of $CH_3$ groups on the surface of $SiO_2$-coated Si NW, via Si—O—Si (silane) bond, showed no improvement in the response signals (FIG. 11B; middle curve), as compared to $SiO_2$-coated Si NW having no $CH_3$ groups. Without being bound by any theory or mechanism of action, this observation might be attributed to an inferior adsorption of hexane molecules in the $CH_3$ layer. Functionalization of $SiO_2$-coated Si NW with longer alkyl chains, such as butyl functional group, showed only minor improvement (FIG. 11B; lower curve). As can be observed from FIG. 11B, exposure of $SiO_2$-coated Si NWs functionalized with butyl chains to 40 ppb hexane showed irreproducible response signals that are within the noise background of the sensor.

In contrast, exposure of non-oxidized alkyl functionalized Si NW FETs to vapor of hexane provided improved, stable, and reproducible responses as well as high signal-to-noise ratio (FIG. 11A). Of note is the lower responses of non-oxidized methyl functionalized (upper curve) Si NW FET in comparison to that of non-oxidized butyl-functionalized (lower curve) Si NW FET, under the same experimental conditions. This could possibly be attributed to the inferior ability of $CH_3$ layer to adsorb vapor analytes, as compared to (longer) butyl chains. Nonetheless, the responses of non-oxidized methyl functionalized Si NW FETs were significantly better than those obtained for oxidized methyl functionalized Si NW FETs.

It is thus evident that the Si NW FETs of the present invention provide enhanced responses in comparison to equivalent $SiO_2$ coated Si NW field effect transistors. Furthermore, the functionalities present in the adsorptive phase play significant role in achieving improved detection levels. Other properties, and in particular the affinity of the functional groups towards analyte molecules, also play important role in producing high sensing capabilities. It is noteworthy that the device presented herein responds at very high sensitivity to minute (40 ppb) quantities of analyte molecules.

Example 9

An Analysis of Complex Multi-Component (Bio) Chemical Media

An array of non-oxidized Si NW FETs, in which each device is functionalized with different organic molecules, namely 2-(4-chlorobutyl)-1,3-dioxolane, 4-chlorobutyl chloroformate, 4-chlorobutyl benzoate, 1-chloro-4-phenylbutane, 4-chlorobutyl acetate, 4-chloro-1-butanol, and $C_3$-$C_8$ alkyl molecules, was prepared according to the principles of the present invention. The array of sensors was exposed to breath patterns simulating either "healthy" breath or "cancerous" patient's breath.

The experiments were performed at ambient conditions using saturated water vapor background flow in order to simulate the background water vapor content of human breath. The simulated "cancerous" breath contained a mixture of 40 ppb isoperene, 37 ppb hexanal, 19 ppb styrene, 15 ppb heptanal, 24 ppb 1,2,4-trimethyl benzene, and 22 ppb decane (Chen et al., *Meas. Sci. Technol.*, 2005, 16, 1535-1546). The simulated "healthy" breath contained a mixture of 26 ppb isoperene, 20 ppb udecane, and 29 ppb decane (Chen et al., *Meas. Sci. Technol.*, 2005, 16, 1535-1546). Multiple exposures to each mixture were performed and data was obtained for the array of sensors. Principal component analysis was performed for the obtained signals.

Figure 12:
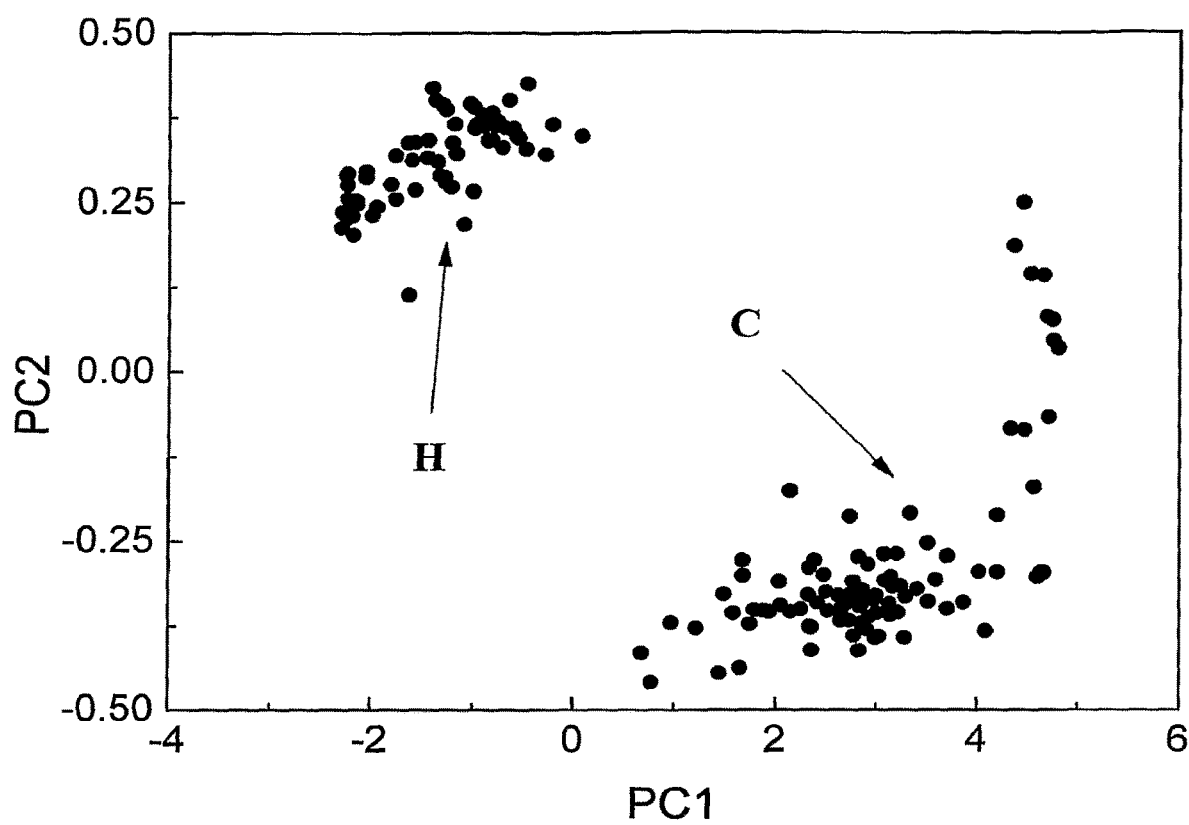
FIG. 12 is a principal components plot of an array of six Si NW field effect transistors upon exposure to simulated "healthy (H)" and "cancerous (C)" breath samples.
Figure 13:
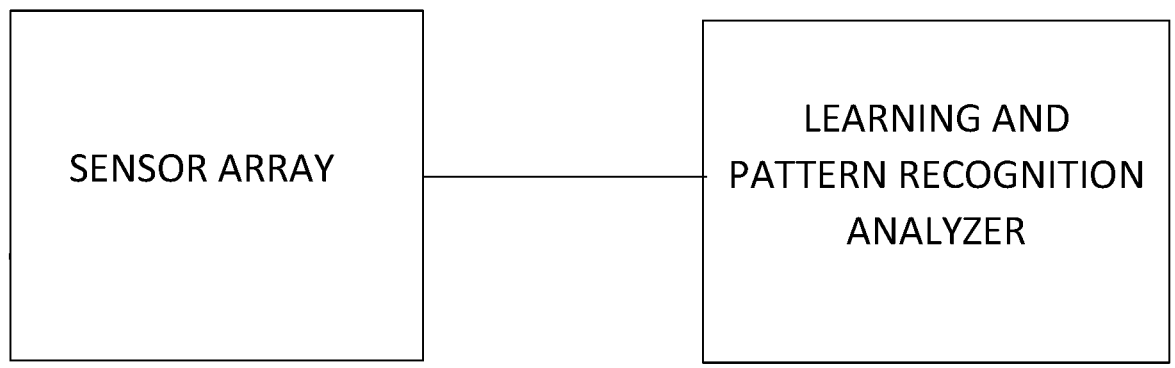
FIG. 13 is a schematic diagram showing the Sensor Array connected to the Learning and Pattern Recognition Analyzer.

FIG. 12 shows a clear discrimination between "cancerous" (C) and "healthy" (H) breath samples using the sensor array of the present invention. Additionally, the discrimination between simulated "healthy" and "cancerous" breath patterns was further improved by increasing the diversity of functionalized, non-oxidized Si NW FETs in the array of sensors. These observations indicate that the developed sensing technology has a high potential for diagnosis, detection, and screening of cancer as well as other diseases via breath samples. The high detection capabilities of the developed electronic nose device render this technology advantageous over the traditional GC-MS that is used in conjugation with a pre-concentration system for similar applications. The devices of the present invention are capable of detecting different volatile biomarkers from breath at ppb level of concentrations.

Example 10

Sensing of Polar and a-Polar Target Molecules

Exposure of non-oxidized butyl-functionalized. Si NW FETs to various a-polar volatile organic compound targets showed correlation between the length of target molecules and the functionality of the Si NW surface. A-polar target molecules (i.e., molecules having approximately zero dipole moment) which possess longer alkyl chains produced smaller electrical responses in absolute value (hexane>heptane>octane). Without being bound by any theory or mechanism of action, the Si NW FETs having a butyl functional group at the monolayer/air interface, provide the adsorption of a-polar target molecules preferably between the butyl chains. The longer the alkyl chain, the lower the adsorption probability between molecular chains resulting in smaller responses (Table 3). Thus, it is presumable that the adsorption of a-polar targets between the molecular chains of the monolayer induces conformational changes in the organic monolayer. These conformational changes affect either the dielectric constant and/or the effective dipole moment of the organic monolayer, which, in turn, affects the conductivity pass through the nanowire.

TABLE 3

Response of non-oxidized butyl-functionalized Silicon NW FETs to various chemical vapors at 40 ppb. The dipole moment values of the different analytes are indicated.

| Analyte | Dipole [D] | Response ($\Delta R/R_b$) |
|---|---|---|
| Hexane | 0 | −0.043 ± 0.04 |
| Heptane | 0 | −0.035 ± 0.04 |
| Octane | 0 | −0.031 ± 0.03 |
| Trichloroethylene | 0.80 | −0.078 ± 0.04 |
| Ethanol | 1.69 | −0.110 ± 0.05 |
| Ethyl acetate | 1.78 | −0.122 ± 0.04 |

The non-oxidized butyl-functionalized Si NW FETs of the present invention were exposed to various polar VOC targets, namely trichloro-ethylene, ethanol, and ethyl acetate (Table 3). A correlation between the Si NW response and the dipole moment of the target molecule was obtained. Target molecules having higher dipole moment values produced higher sensor responses in absolute value. Without being bound by any theory or mechanism of action, the higher responses of polar molecules, with respect to a-polar molecules indicate that the sensing process of polar molecules involves at least one additional mechanism. This observation might be attributed to either one of the following scenarios. In the first scenario, the polar molecules adsorb on/in the monolayer close to the NW surface and induce direct electrostatic interaction with the NW charge carriers. In the second scenario, the target molecules change the dielectric constant and/or effective dipole moment of the organic monolayer, thus affecting the NW conductivity. It is thus concluded that minute concentrations of polar VOCs are capable of producing large electronic responses of in non-oxidized butyl-functionalized Si NW FETs.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. In an electronic device comprising an array of chemically sensitive sensors for detecting volatile organic compounds in a sample, the chemically sensitive sensors comprising field effect transistors comprising functionalized silicon nanowires, the improvement wherein:
    said field effect transistors are non-oxidized functionalized silicon nanowires comprising surface Si atoms and a plurality of functional groups, which form a direct Si—C bond with the silicon nanowires, wherein Si is a surface Si atom and C is a carbon atom of the functional group, wherein the plurality of functional groups are selected from the group consisting of propyl, pentyl, hexyl, octyl, decyl, and undecyl, and wherein coverage of the surface Si atoms by said plurality of functional groups is at least about 50%.

2. In a system comprising an electronic device comprising an array of chemically sensitive sensors for detecting volatile organic compounds in a sample, the chemically sensitive sensors comprising field effect transistors comprising functionalized silicon nanowires, wherein said chemically sensitive sensors output sensor output signals, and a learning and pattern recognition analyzer that receives the sensor output signals from said electronic device and analyzes the signals to produce an output signature, the improvement wherein said electronic device is an electronic device in accordance with claim 1.

3. The system according to claim 2, wherein the learning and pattern recognition analyzer comprises at least one algorithm selected from the group consisting of principal component analysis (PCA), artificial neural network algorithms, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

4. The electronic device according to claim 1, wherein said chemically sensitive sensors output sensor output signals.

* * * * *